(12) United States Patent
Makings et al.

(10) Patent No.: US 7,820,817 B2
(45) Date of Patent: Oct. 26, 2010

(54) MODULATORS OF MUSCARINIC RECEPTORS

(75) Inventors: Lewis Makings, Encinitas, CA (US); Dennis Hurley, San Marcos, CA (US); Miguel Gracia-Guzman Blanco, San Diego, CA (US); Daniele Bergeron, La Mesa, CA (US); Akiko Nakatani, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1053 days.

(21) Appl. No.: 11/140,808

(22) Filed: May 31, 2005

(65) Prior Publication Data

US 2006/0019962 A1 Jan. 26, 2006

Related U.S. Application Data

(60) Provisional application No. 60/575,233, filed on May 28, 2004.

(51) Int. Cl.
*C07D 403/00* (2006.01)
*C07D 241/02* (2006.01)
*C07D 401/00* (2006.01)
*C07D 211/32* (2006.01)

(52) U.S. Cl. .............. 544/295; 544/357; 544/360; 546/199

(58) Field of Classification Search .......... None
See application file for complete search history.

(56) References Cited

U.S. PATENT DOCUMENTS

| | | | |
|---|---|---|---|
| 2004/0122018 A1 | 6/2004 | Zhu et al. | |
| 2004/0137062 A1 | 7/2004 | Chopra | |
| 2004/0209878 A1 | 10/2004 | Guzi et al. | |
| 2004/0209887 A1 | 10/2004 | Fu | |
| 2004/0229908 A1 | 11/2004 | Nelson | |
| 2004/0265238 A1 | 12/2004 | Chaudry | |
| 2005/0008702 A1 | 1/2005 | Faour et al. | |
| 2005/0015039 A1 | 1/2005 | Salzwedel et al. | |
| 2005/0019412 A1 | 1/2005 | Bosch et al. | |
| 2005/0020548 A1 | 1/2005 | Allaway et al. | |
| 2005/0025761 A1 | 2/2005 | Thorpe et al. | |
| 2005/0026902 A1 | 2/2005 | Maziasz | |
| 2005/0031620 A1 | 2/2005 | Thorpe et al. | |
| 2005/0031713 A1 | 2/2005 | Ehrich et al. | |
| 2005/0032794 A1 | 2/2005 | Padia et al. | |
| 2005/0048002 A1 | 3/2005 | Rabinow et al. | |
| 2005/0049256 A1 | 3/2005 | Lorton et al. | |
| 2005/0055078 A1 | 3/2005 | Campbell | |
| 2005/0058696 A1 | 3/2005 | Donello et al. | |
| 2005/0059023 A1 | 3/2005 | Cantor | |
| 2005/0059578 A1 | 3/2005 | Thorpe et al. | |
| 2005/0059744 A1 | 3/2005 | Donello et al. | |
| 2005/0065124 A1 | 3/2005 | Adorini et al. | |
| 2005/0074425 A1 | 4/2005 | Waugh et al. | |
| 2005/0074487 A1 | 4/2005 | Hsu et al. | |
| 2005/0075326 A1 | 4/2005 | Chan Chun Kong et al. | |
| 2005/0079200 A1 | 4/2005 | Rathenow et al. | |
| 2005/0079201 A1 | 4/2005 | Rathenow et al. | |
| 2005/0085463 A1 | 4/2005 | Weiner et al. | |

FOREIGN PATENT DOCUMENTS

| | | |
|---|---|---|
| WO | WO 9614297 | 5/1996 |
| WO | WO 0006153 | 2/2000 |
| WO | WO 0014089 | 3/2000 |
| WO | WO 0042852 | 7/2000 |
| WO | WO 0121577 | 3/2001 |
| WO | WO 0164213 | 9/2001 |
| WO | WO 2004010942 | 2/2004 |
| WO | WO 2004010943 | 2/2004 |
| WO | WO 2004011427 | 2/2004 |
| WO | WO 2005013937 | 2/2005 |
| WO | WO 2005016310 | 2/2005 |
| WO | WO 2005018530 | 3/2005 |

OTHER PUBLICATIONS

Dorwald F. A. Side Reactions in Organic Synthesis, 2005, Wiley: VCH, Weinheim p. IX of Preface.*

* cited by examiner

*Primary Examiner*—James O Wilson
*Assistant Examiner*—Jeffrey H Murray
(74) *Attorney, Agent, or Firm*—Honigman Miller Schwartz and Cohn LLP

(57) ABSTRACT

The present invention relates to substituted piperazine compounds that are useful modulators of muscarinic receptors. The present invention also provides compositions comprising such compounds, and methods for treating muscarinic receptor mediated diseases.

29 Claims, No Drawings

MODULATORS OF MUSCARINIC RECEPTORS

CROSS-REFERENCE

This application claims priority under 35 U.S.C. §119(e) to U.S. Ser. No. 60/575,233 filed on May 28, 2004, the entire contents of which are incorporated herein by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," *J. Med. Chem.*, 43(23), pp. 4333-4353 (2000); Hulme, E. C. et al., "Muscarinic Receptor Subtypes," *Ann. Rev. Pharmacol. Toxicol.*, 30, pp. 633-673 (1990); Caulfield, M. P. et al., "Muscarinic Receptors—Characterization, Coupling, and Function," *Pharmacol. Ther.*, 58, pp. 319-379 (1993); Caulfield, M. P. et al., International Union of Pharmacology. XVII. Classification of Muscarinic Acetylcholine Receptors," *Pharmacol. Rev.*, 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors), and Pain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain on the other had may last for much longer periods of time and it's intensity is more graded. Inflammation may occur for many reasons including tissue damage, autoimmune response, and pathogen invasion. Inflammatory pain is mediated by an "inflammatory soup" that consists of substance P, histamines, acid, prostaglandin, bradykinin, CGRP, cytokines, ATP, and neurotransmitter release. The third class of pain is neuropathic and involves nerve damage that results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX2 inhibitors, opioids, tricyclic antidepressants, and anticonvulsants. Neuropathic pain has been particularly difficult to treat as it does not respond well to opiods until high doses are reached. Gabapentin is currently the favored therapeutic for the treatment of neuropathic pain although it works in only 60% of patients where it shows modest efficacy. The drug is however very safe and side effects are generally tolerable although sedation is an issue at higher doses.

Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides compounds of formula (I) useful in modulating activity of a muscarinic receptor:

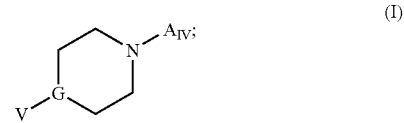

wherein V, G, x and A are defined herein.

The present invention also provides compositions comprising compounds of formula (I), and methods of treating muscarinic receptor mediated diseases using compounds of formula (I).

DETAILED DESCRIPTION OF THE INVENTION

I. Definitions

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

The phrase "optionally substituted" is used interchangeably with the phrase "substituted or unsubstituted." As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. As one of ordinary skill in the art will recognize, combinations of substituents envisioned by this invention are those combinations that result in the formation of stable or chemically feasible compounds.

The term "aliphatic" or "aliphatic group", as used herein, means a straight-chain or branched, substituted or unsubstituted hydrocarbon chain that is completely saturated (alkyl) or is unsaturated (alkenyl or alkynyl). Unless otherwise specified, an aliphatic group has 1 to 12 carbon atoms, preferably, 1-6 carbon atoms, and more preferably, 1-4 carbon atoms. Up to three, and preferably two, —$CH_2$— in said aliphatic may be replaced with O, S, or —NR.

The term "cycloaliphatic" means a saturated or partially unsaturated monocyclic or bicyclic hydrocarbon ring that has a single point of attachment to the rest of the molecule. Unless otherwise specified, preferred cycloaliphatic rings are 3-8 membered monocyclic rings, more preferably 3-6, and even more preferably, 3, 5, or 6. Also preferred, unless otherwise specified, are 8-12 membered bicyclic hydrocarbon rings, more preferably 10 membered bicyclic hydrocarbon rings.

The term "heteroatom," unless otherwise specified, means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or as in N-substituted pyrrolidinyl.

The term "unsaturated", as used herein, means a double bond or a triple bond. Each such bond constitutes one unit of unsaturation.

The term "aryl" used alone or as part of a larger moiety as in "aralkyl", "aralkoxy", or "aryloxyalkyl", refers to monocyclic, bicyclic and tricyclic aromatic carbocyclic ring systems. Unless otherwise specified, preferred aryl rings have a total of five to fourteen ring members, wherein at least one ring, if bicyclic or tricyclic, in the system is aromatic and wherein each ring in the system contains up to 6 ring members. The term "aryl" may be used interchangeably with the term "aryl ring". Phenyl is an example of aryl.

The term "heterocycle", "heterocyclyl", or "heterocyclic" as used herein means non-aromatic, monocyclic, bicyclic or tricyclic ring systems wherein one or more ring members is a heteroatom. Unless otherwise specified, each ring in the system preferably contains 3 to 7 ring members with preferably 1-3 heteroatoms.

The term "heteroaryl", used alone or as part of a larger moiety as in "heteroaralkyl" or "heteroarylalkoxy", refers to monocyclic, bicyclic and tricyclic ring systems, wherein at least one ring in the system is aromatic, and at least one ring in the system contains one or more heteroatoms. Unless otherwise specified, such ring systems preferably have a total of 5 to 15 ring members, wherein each ring in the system preferably contains 3 to 7 ring members, with preferably 1-3 heteroatoms. The term "heteroaryl" may be used interchangeably with the term "heteroaryl ring" or the term "heteroaromatic".

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

As used herein, the term "protecting group" refers to organic substituents used to protect a chemical functionality from reacting with reagents and reactants during chemical synthesis. Various "protecting groups" are known. See, e.g., T. W. Greene & P. G. M Wutz, "Protective Groups in Organic Synthesis," 3$^{rd}$ Edition, John Wiley & Sons, Inc. (1999) along with any other editions of this book.

Unless otherwise stated, structures depicted herein are also meant to include all stereochemical forms of the structure including, e.g., endo, exo, R and S configurations. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen atom by a deuterium or tritium, or the replacement of a carbon by a $^{13}C$- or $^{14}C$-enriched carbon are within the scope of this invention. Such compounds are useful, for example, as analytical tools or probes in biological assays.

II. Compounds

The present invention provides compounds of formula (I) useful in modulating activity of a muscarinic receptor:

(I)

wherein:

V is a 5-6 membered unsaturated, monocyclic, heterocyclic ring containing 1-4 ring heteroatoms selected from O, S, and N, or a 5-15 membered heteroaromatic ring containing 1-4 ring heteroatoms selected from O, S, and N, in which the 5-6 membered unsaturated, monocyclic, heterocyclic ring and the 5-15 membered heteroaromatic ring are optionally substituted with 1 to 3 substituents selected from $R^1$, $R^2$, $R^3$, $R^4$, or $R^5$;

G is N or $CR^x$;

$R^x$ is H, halo, CN, $R^2$, $OR^6$, —$(CH_2)_wOC(O)R^2$, $C(O)OR^2$, $C(O)NH_2$, $C(O)NHR^2$, or $C(O)N(R^2)_2$;

A is selected from:

(i)

(ii)

(iii)

(iv)

or A is adamantyl or adamantylmethyl;

wherein:

bond r is a single or double bond;

when ring B is present, then bond r is fused with B;

each of $X_1$, $X_3$ and $X_4$ is independently selected from $CH_2$, $CH_2$—$CH_2$, O, S, $SO_2$, NR, wherein R is $R^2$ or $R^4$;

$X_2$ is CH;

each of $W_1$, $W_3$, and $W_4$ is independently selected from a bond, —$(CH2)_i$-, —$(CH_2)_iNR^iC(O)$—, —$(CH_2)_iC(O)NR^i$—, —$(CH_2)_iNR^iSO_2$—, —$(CH_2)_iSO_2NR^i$—, C(O), O, S, NH, or $S(O)_2$;

$R^i$ is H or $R_2$;

$W_2$ and $X_2$ taken together are selected from CH, $CH_2$—CH, —$(CH_2)_iC(O)N$—, or —$(CH_2)_iSO_2N$—;

ring B, when present, is a 5-6 membered cycloaliphatic or 5-6 membered heterocyclic ring, in which the 5-6 membered cycloaliphatic or 5-6 membered heterocyclic ring are each optionally substituted with 1 to 3 substituents selected from $R^1$, $R^2$, $R^3$, $R^4$, or $R^5$;

$R^1$ is oxo or ((C1-C4)aliphatic)$_p$-Y;

Y is halo, CN, $NO_2$, $CF_3$, $OCF_3$, OH, $SR^6$, $S(O)R^6$, $SO_2R^6$, COOH, $COOR^6$ or $OR^6$; or $R^2$ is aliphatic, wherein each $R^2$ optionally includes 1 to 2 substituents independently selected from $R^1$, $R^4$, or $R^5$;

$R^3$ is a cycloaliphatic, aryl, heterocyclic, or heteroaryl ring optionally including 1 to 3 substituents independently selected from $R^1$, $R^2$, $R^4$, or $R^5$;

$R^4$ is $OR^5$, $OR^6$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;

$R^5$ is a cycloaliphatic, aryl, heterocyclic, or heteroaryl ring, optionally including 1 to 3 $R^1$ substituents;

$R^6$ is H or aliphatic, wherein $R^6$ optionally includes a $R^7$ substituent;

$R^7$ is a cycloaliphatic, aryl, heterocyclic, or heteroaryl ring, and each $R^7$ optionally comprises up to 2 substituents independently chosen from H, ($C_1$-$C_6$)-straight or branched alkyl, ($C_2$-$C_6$) straight or branched alkenyl or alkynyl, 1,2-methylenedioxy, 1,2-ethylenedioxy, or $(CH_2)_n$—Z;

Each $R^8$ is selected from $R^2$; $R^3$, or $R^4$ or a protecting group. Z is selected from halo, CN, $NO_2$, $CF_3$, $OCF_3$, OH, S-aliphatic, S(O)-aliphatic, $SO_2$-aliphatic, $NH_2$, NH-aliphatic, N(aliphatic)$_2$, COOH, C(O)O(-aliphatic), or O-aliphatic;

Each i is independently 1-3;

Each m is independently 1 or 2;

Each n is independently 0 or 1;

Each p is independently 0 or 1;

Each w is independently 0 or 1;

Each x is independently 1 or 2; and with the proviso that the following compounds are not included:

2-(4-bicyclo[2.2.1]hept-2-yl-1-piperazinyl)-pyrimidine;

2-[4-(bicyclo[2.2.1]hept-5-en-2-ylmethyl)-1-piperazinyl]-pyrimidine;

3-(1-bicyclo[2.2.1]hept-2-yl-4-piperidinyl)-2(3H)-benzoxazolone;

1-[1-[(1R,2R,4S)bicyclo[2.2.1]hept-2-ylmethyl]-4-piperidinyl]-1,3-dihydro-2H-indol-2-one;

1-(1-bicyclo[2.2.1]hept-2-yl-4-piperidinyl)-3-ethylidene-1,3-dihydro-2H-indol-2-one;

1-(4-amino-6,7-dimethoxy-2-quinazolinyl)-4-[(tetrahydro-3,5-methano-2H-cyclopenta[b]furan-3(3aH)-yl)carbonyl]-piperazine;

1-(1-bicyclo[2.2.1]hept-2-yl-4-piperidinyl)-3,4-dihydro-2(1H)-quinolinone;

5-(1-bicyclo[2.2.1]hept-2-yl-4-piperidinyl)-3-bromo-N-(3-pyridinylmethyl)-pyrazolo[1,5-a]pyrimidin-7-amine;

1-(1-bicyclo[2.2.1]hept-2-yl-4-piperidinyl)-3-ethyl-1,3-dihydro-2H-indol-2-one;

1-(1-bicyclo[2.2.1]hept-2-yl-4-piperidinyl)-3,4-dihydro-2,2-dioxide-1H-2,1,3-benzothiadiazine;

1-(1-bicyclo[2.2.1]hept-2-yl-4-piperidinyl)-1,3-dihydro-2H-indol-2-one;

1-[1-[(1R,2S,4S)-bicyclo[2.2.1]hept-2-ylmethyl]-4-piperidinyl]-1,3-dihydro-2H-indol-2-one;

[1-(1-bicyclo[2.2.1]hept-2-yl-4-piperidinyl)-3-ethyl-1,3-dihydro-2H-benzimidazol-2-ylidene]-cyanamide;

1-(4-amino-6,7-dimethoxy-2-quinazolinyl)-4-(bicyclo[2.2.1]hept-5-en-2-ylcarbonyl)-piperazine;

5-(1-bicyclo[2.2.1]hept-2-yl-4-piperidinyl)-3-bromo-N-(3-pyridinylmethyl)-pyrazolo[1,5-a]pyrimidin-7-amine;

1-[1-[(1R,2R,4S)-bicyclo[2.2.1]hept-2-ylmethyl]-4-piperidinyl]-1,3-dihydro-2H-indol-2-one;

1-[1-[(1R,2S,4S)-bicyclo[2.2.1]hept-2-ylmethyl]-4-piperidinyl]-1,3-dihydro-2H-indol-2-one;

3-(1-bicyclo[2.2.1]hept-2-yl-4-piperidinyl)-2(3H)-benzoxazolone;

1-(1-bicyclo[2.2.1]hept-2-yl-4-piperidinyl)-1,3-dihydro-2H-Indol-2-one;

1-(1-bicyclo[2.2.1]hept-2-yl-4-piperidinyl)-3-ethylidene-1,3-dihydro-2H-Indol-2-one;

1-(1-bicyclo[2.2.1]hept-2-yl-4-piperidinyl)-3-ethyl-1,3-dihydro-2H-indol-2-one;

1-(1-bicyclo[2.2.1]hept-2-yl-4-piperidinyl)-3,4-dihydro-2,2-dioxide-1H-2,1,3-benzothiadiazine; and 1-(1-bicyclo[2.2.1]hept-2-yl-4-piperidinyl)-3,4-dihydro-2(1H)-quinolinone.

According to another aspect, the present invention provides a compound having formula (II):

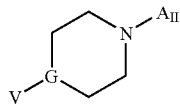

II

Wherein ring $A_{II}$ is selected from:

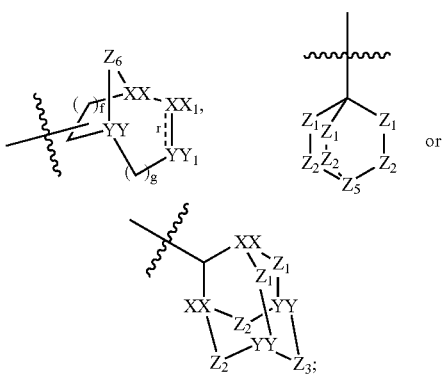

Each XX, YY, and $Z_5$ is independently CR' or N;

Each $XX_1$ and $YY_1$ is independently selected from a bond, $CH_2$, $CHR^{90}$, O, S; NH, NR', C(O), S(O), or $SO_2$ provided that both $X_1$ and $Y_1$ are not simultaneously a bond;

when $XX_1$ and $YY_1$ are each $CHR^{90}$, then the two $R^{90}$ together with the atoms to which they are attached may form a 5 to 8 membered cycloaliphatic or heterocyclic fused ring.

Each $Z_6$ is independently —C(R')$_2$—, —C(R')$_2$—C(R')$_2$—, —C(R')$_2$—Q—, or Q, wherein Q is O, —N(R')—, —S(O)—, —SO$_2$—, or —C(O)—;

Each $Z_1$, $Z_2$, $Z_3$, and $Z_4$ is independently selected from $CH_2$, CHR', O, S, NH, NR', C(O), S(O), $SO_2$;

Each R' is independently selected from (C1-C4)aliphatic)$_{mm}$-$Q^1$, S(O)$_i$$R^{60}$, S(O)$_i$$R^{50}$, $SO_2N(R^{60})_2$, $SO_2N(R^{50})_2$, $SO_2NR^{50}R^{60}$C(O)$R^{50}$, C(O)OR$^{50}$, C(O)R$^{60}$, C(O)OR$^{60}$, C(O)N(R$^{60}$)$_2$, C(O)N(R$^{50}$)$_2$, C(O)N(R$^{50}$R$^{60}$), C(O)N(OR$^{60}$)R$^{60}$, C(O)N(OR$^{50}$)R$^{60}$, C(O)N(OR$^{60}$)R$^{50}$, C(O)N(OR$^{50}$)R$^{50}$, C(NOR$^{60}$)R$^{60}$, C(NOR$^{60}$)R$^{50}$, C(NOR$^{50}$)R$^{60}$, C(NOR$^{50}$)R$^{50}$, R$^{20}$, or R$^{60}$, provided that when any of $XX_1$, $YY_1$, $Z_6$, $Z_1$, $Z_2$, $Z_3$, and $Z_4$ are NR', then R' is S(O)$_i$R$^{60}$, S(O)$_i$R$^{50}$, $SO_2N(R^{60})_2$, $SO_2N(R^{50})_2$, $SO_2NR^{50}R^{60}$, C(O)R$^{50}$, C(O)OR$^{50}$, C(O)R$^{60}$, C(O)OR$^{60}$, C(O)N(R$^{60}$)$_2$, C(O)N(R$^{50}$)$_2$, C(O)N(R$^{50}$R$^{60}$), C(O)N(OR$^{60}$)R$^{60}$, C(O)N(OR$^{50}$)R$^{60}$, C(O)N(OR$^{60}$)R$^{50}$, C(O)N(OR$^{50}$)R$^{50}$, C(NOR$^{60}$)R$^{60}$, C(NOR$^{60}$)R$^{50}$, C(NOR$^{50}$)R$^{60}$, or C(NOR$^{50}$)R$^{50}$;

Each $R^{10}$ is independently oxo or ((C1-C4)aliphatic)$_{mm}$-$Q^1$;

Each $Q^1$ is independently halo, CN, $NO_2$, $CF_3$, $OCF_3$, OH, $SR^{60}$, S(O)$R^{60}$, $SO_2R^{60}$, COOH, COOR$^{60}$ or OR$^{60}$;

Each $R^{20}$ is independently aliphatic optionally substituted with 1-3 substituents independently selected from $R^{10}$, $R^{40}$, or $R^{50}$;

Each $R^{30}$ is independently a cycloaliphatic, aryl, heterocyclic, or heteroaryl ring, wherein each of the cycloaliphatic, aryl, heterocyclic, or heteroaryl are optionally substituted with 1-3 substituents independently selected from $R^{10}$, $R^{20}$, $R^{40}$, or $R^{50}$;

Each $R^{40}$ is independently OR$^{50}$, OR$^{60}$, OC(O)R$^{60}$, OC(O)R$^{50}$, OC(O)OR$^{60}$, OC(O)OR$^{50}$, OC(O)N(R$^{60}$)$_2$, OC(O)N(R$^{50}$)$_2$, OC(O)N(R$^{60}$R$^{50}$), S(O)$_i$R$^{60}$, S(O)$_i$R$^{50}$, $SO_2N(R^{60})_2$, $SO_2N(R^{50})_2$, $SO_2NR^{50}R^{60}$, C(O)R$^{50}$, C(O)OR$^{50}$, C(O)R$^{60}$, C(O)OR$^{60}$, C(O)N(R$^{60}$)$_2$, C(O)N(R$^{50}$)$_2$, C(O)N(R$^{50}$R$^{60}$), C(O)N(OR$^{60}$)R$^{60}$, C(O)N(OR$^{50}$)R$^{60}$, C(O)N(OR$^{60}$)R$^{50}$, C(O)N(OR$^{50}$)R$^{50}$, C(NOR$^{60}$)R$^{60}$, C(NOR$^{50}$)R$^{60}$, C(NOR$^{60}$)R$^{50}$, C(NOR$^{50}$)R$^{50}$, NR$^{50}$C(O)R$^{50}$, NR$^{60}$C(O)R$^{60}$, NR$^{60}$C(O)R$^{50}$, NR$^{60}$C(O)OR$^{60}$, NR$^{50}$C(O)OR$^{60}$, NR$^{60}$C(O)OR$^{50}$, NR$^{50}$C(O)OR$^{50}$, NR$^{60}$C(O)N(R$^{60}$)$_2$, NR$^{60}$C(O)NR$^{50}$R$^{60}$, NR$^{60}$C(O)N(R$^{50}$)$_2$, NR$^{50}$C(O)N(R$^{60}$)$_2$, NR$^{50}$C(O)NR$^{50}$R$^{60}$, NR$^{50}$C(O)N(R$^{50}$)$_2$, NR$^{60}$SO$_2$R$^{60}$, NR$^{60}$SO$_2$R$^{50}$, NR$^{50}$SO$_2$R$^{50}$, NR$^{60}$SO$_2$N(R$^{60}$)$_2$, NR$^{60}$SO$_2$NR$^{50}$R$^{60}$, NR$^{60}$SO$_2$N(R$^{50}$)$_2$, NR$^{50}$SO$_2$NR$^{50}$R$^{60}$, NR$^{50}$SO$_2$N(R$^{50}$)$_2$, N(OR$^{60}$)R$^{60}$, N(OR$^{60}$)R$^{50}$, N(OR$^{50}$)R$^{50}$, or N(OR$^{50}$)R$^{60}$;

Each $R^{50}$ is independently a cycloaliphatic, aryl, heterocyclic, or heteroaryl ring, wherein each of the cycloaliphatic, aryl, heterocyclic, or heteroaryl are optionally substituted with 1 to 3 of $R^{10}$;

Each $R^{60}$ is independently H or aliphatic optionally substituted with $R^{70}$;

Each $R^{70}$ is independently a cycloaliphatic, aryl, heterocyclic, or heteroaryl ring, wherein each of the cycloaliphatic, aryl, heterocyclic, or heteroaryl are optionally substituted with 1 to 2 of ($C_1$-$C_6$)-straight or branched alkyl, ($C_2$-$C_6$) straight or branched alkenyl or alkynyl, 1,2-methylenedioxy, 1,2-ethylenedioxy, or $(CH_2)_{nn}$-$Q^2$;

Each $Q^2$ is independently selected from halo, CN, $NO_2$, $CF_3$, $OCF_3$, OH, S-aliphatic, S(O)-aliphatic, $SO_2$-aliphatic, COOH, C(O)O-aliphatic, or O-aliphatic;

bond r is a single or double bond;
Each $R^{80}$ is independently an amino protecting group;
Each $R^{90}$ is independently $R^2$, $R^3$, or $R^6$;
Each ii is independently 0, 1, 2, or 3;
Each mm is independently 0 or 1;
Each nn is independently 0 or 1;
Each f is 0, 1 or 2; and
Each g is 0, 1 or 2, with the proviso that the following compounds are not included:

2-(4-bicyclo[2.2.1]hept-2-yl-1-piperazinyl)-pyrimidine;
2-[4-(bicyclo[2.2.1]hept-5-en-2-ylmethyl)-1-piperazinyl]-pyrimidine;
3-(1-bicyclo[2.2.1]hept-2-yl-4-piperidinyl)-2(3H)-benzoxazolone;
1-[1-[(1R,2R,4S)-bicyclo[2.2.1]hept-2-ylmethyl]-4-piperidinyl]-1,3-dihydro-2H-indol-2-one;
1-(1-bicyclo[2.2.1]hept-2-yl-4-piperidinyl)-3-ethylidene-1,3-dihydro-2H-indol-2-one;
1-(4-amino-6,7-dimethoxy-2-quinazolinyl)-4-[(tetrahydro-3,5-methano-2H-cyclopenta[b]furan-3(3aH)-yl)carbonyl]-piperazine;
1-(1-bicyclo[2.2.1]hept-2-yl-4-piperidinyl)-3,4-dihydro-2(1H)-quinolinone;
5-(1-bicyclo[2.2.1]hept-2-yl-4-piperidinyl)-3-bromo-N-(3-pyridinylmethyl)-pyrazolo[1,5-a]pyrimidin-7-amine;
1-(1-bicyclo[2.2.1]hept-2-yl-4-piperidinyl)-3-ethyl-1,3-dihydro-2H-indol-2-one;
1-(1-bicyclo[2.2.1]hept-2-yl-4-piperidinyl)-3,4-dihydro-2,2-dioxide-1H-2,1,3-benzothiadiazine;
1-(1-bicyclo[2.2.1]hept-2-yl-4-piperidinyl)-1,3-dihydro-2H-indol-2-one;
1-[1-[(1R,2S,4S)-bicyclo[2.2.1]hept-2-ylmethyl]-4-piperidinyl]-1,3-dihydro-2H-indol-2-one;
1-(1-bicyclo[2.2.1]hept-2-yl-4-piperidinyl)-3-ethyl-1,3-dihydro-2H-benzimidazol-2-ylidene-cyanamide;
1-(4-amino-6,7-dimethoxy-2-quinazolinyl)-4-(bicyclo[2.2.1]hept-5-en-2-ylcarbonyl)-piperazine;
5-(1-bicyclo[2.2.1]hept-2-yl-4-piperidinyl)-3-bromo-N-(3-pyridinylmethyl)-pyrazolo[1,5-a]pyrimidin-7-amine;
1-[1-[(1R,2R,4S)-bicyclo[2.2.1]hept-2-ylmethyl]-4-piperidinyl]-1,3-dihydro-2H-indol-2-one;
1-[1-[(1R,2S,4S)-bicyclo[2.2.1]hept-2-ylmethyl]-4-piperidinyl]-1,3-dihydro-2H-indol-2-one;
3-(1-bicyclo[2.2.1]hept-2-yl-4-piperidinyl)-2(3H)-benzoxazolone;
1-(1-bicyclo[2.2.1]hept-2-yl-4-piperidinyl)-1,3-dihydro-2H-Indol-2-one;
1-(1-bicyclo[2.2.1]hept-2-yl-4-piperidinyl)-3-ethylidene-1,3-dihydro-2H-indol-2-one;
1-(1-bicyclo[2.2.1]hept-2-yl-4-piperidinyl)-3-ethyl-1,3-dihydro-2H-indol-2-one;
1-(1-bicyclo[2.2.1]hept-2-yl-4-piperidinyl)-3,4-dihydro-2,2-dioxide-1H-2,1,3-benzothiadiazine; and
1-(1-bicyclo[2.2.1]hept-2-yl-4-piperidinyl)-3,4-dihydro-2(1H)-quinolinone.

According to another embodiment, the present invention provides compounds of formula (III):

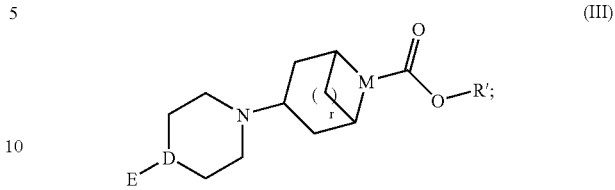

wherein:
r is 0-3;
M is N or CH;
E is a 3-6 membered unsaturated or aromatic, monocyclic, heterocyclic ring containing 1-3 ring nitrogen heteroatoms, or E is

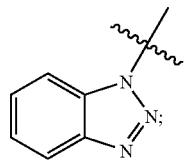

wherein E is optionally substituted with up to four substituents independently selected from $R^1$, $R^2$, $R^3$, $R^4$, or $R^5$;
D is N or CR";
R" is H, halo, CN, $R^2$, $OR^6$, $-(CH_2)_wOC(O)R^2$, $C(O)OR^2$, $C(O)NH_2$, $C(O)NHR^2$, or $C(O)N(R^2)_2$;
R' is $R^2$;
x is 1 or 2;
wherein p, Y, $R^1$, $R^2$, $R^3$, $R^4$ and $R^5$ are as defined above in formula (I);

provided that:
(i) when D is N, R' is t-butyl, then E is not 5-cyano-4-[(2,4-difluorophenyl)methyl]amino-2-pyrimidinyl;
(ii) when D is N, R' is t-butyl, then E is not 5-ethoxycarbonyl-2-pyrimidinyl or pyridine-2-yl-5-carboxylic acid;
(iii) when D is CH, R' is methyl, then E is not 3-amino-2-pyridinyl;
(iv) when D is N, R' is t-butyl, then E is not 5-carboxy-4-(1-methyethyl)-2-thiazolyl; or
(v) when D is N, R' is ethyl, then E is not 4-chloro-1,2,5-thiadiazol-3-yl.

According to another embodiment, the present invention provides compounds of formula (IV):

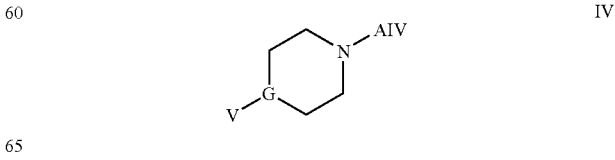

or a pharmaceutically acceptable salt thereof, wherein $A_{IV}$ is adamantanyl, adamantanylmethyl, or

[structure diagram showing W₁ connected to ring with X₁ and m, r substituents]

Bond r is a single or double bond;

Each $X_1$ is independently selected from $CH_2$, $CH_2$—$CH_2$, or $NR^{400}$,

Each $W_1$ is independently selected from a bond, —(CH2)$_i$-, —(CH$_2$)$_i$NR$^i$C(O)—, —(CH$_2$)$_i$C(O)NR$^i$—, —(CH$_2$)$_i$NR$^i$SO$_2$—, —(CH$_2$)$_i$SO$_2$NR$^i$—, C(O), O, S, NH, or S(O)$_2$;

$R^i$ is H or $R^2$;

$R^2$ is aliphatic, wherein each $R^2$ optionally includes 1 to 2 substituents independently selected from $R^{100}$, $R^4$, or $R^5$;

$R^4$ is OR$^5$, OR$^6$, S(O)R$^6$, S(O)R$^5$, SO$_2$R$^6$, SO$_2$R$^5$, SO$_2$N(R$^6$)$_2$, SO$_2$N(R$^5$)$_2$, SO$_2$NR$^5$R$^6$, SO$_3$R$^6$, SO$_3$R$^5$, C(O)R$^5$, C(O)OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^6$, C(O)N(OR$^5$)R$^6$, C(O)N(OR$^6$)R$^5$, C(O)N(OR$^5$)R$^5$, C(NOR$^5$)R$^6$, C(NOR$^6$)R$^5$, C(NOR$^5$)R$^6$, C(NOR$^5$)R$^5$, NR$^5$C(O)R$^5$, NR$^6$C(O)R$^6$, NR$^6$C(O)R$^5$, NR$^6$C(O)OR$^6$, NR$^5$C(O)OR$^6$, NR$^6$C(O)OR$^5$, NR$^5$C(O)OR$^5$, NR$^6$C(O)N(R$^6$)$_2$, NR$^6$C(O)NR$^5$R$^6$, NR$^6$C(O)N(R$^5$)$_2$, NR$^5$C(O)N(R$^6$)$_2$, NR$^5$C(O)NR$^5$R$^6$, NR$^5$C(O)N(R$^5$)$_2$, NR$^6$SO$_2$R$^6$, NR$^6$SO$_2$R$^5$, NR$^5$SO$_2$R$^5$, NR$^6$SO$_2$N(R$^6$)$_2$, NR$^6$SO$_2$NR$^5$R$^6$, NR$^6$SO$_2$N(R$^5$)$_2$, NR$^5$SO$_2$NR$^5$R$^6$, NR$^5$SO$_2$N(R$^5$)$_2$, N(OR$^6$)R$^6$, N(OR$^6$)R$^5$, N(OR$^5$)R$^5$, or N(OR$^5$)R$^6$;

Each $R^5$ is independently a cycloaliphatic, aryl, heterocyclic, or heteroaryl ring, each optionally including 1 to 3 $R^{100}$ substituents;

Each $R^6$ is independently H or aliphatic optionally substituted with $R^7$;

Each $R^7$ is independently a cycloaliphatic, aryl, heterocyclic, or heteroaryl ring, each optionally substituted with up to 2 substituents independently selected from H, (C$_1$-C$_6$)-straight or branched alkyl, (C$_2$-C$_6$) straight or branched alkenyl or alkynyl, 1,2-methylenedioxy, 1,2-ethylenedioxy, or (CH$_2$)$_n$—Z;

Each $R^8$ is independently selected from $R^2$, $R^3$, or $R^4$ or a protecting group.

Each Z is independently selected from halo, —CN, —NO$_2$, —CF$_3$, —OCF$_3$, —OH, —S-aliphatic, —S(O)-aliphatic, —SO$_2$-aliphatic, —COOH, —C(O)O(-aliphatic), or —O-aliphatic;

G is N or C(H);

V is

[two structure diagrams: one showing a ring with Z1-Z6 positions, and a benzotriazole]

in which the benzotriazole is optional substituted with 1-3 of $R^{100}$, R2, R4, R5, or R6;

Each Z1 and Z3 is independently —N═, —C(H)═, or —C(R$_{100}$)═;

Each Z2 is independently a carbon atom;

Each Z4 and Z6 is independently —N═, —C(H)═ or —C(R$_{100}$)═;

Each Z5 is independently —N═, —C(H)═, or —C(R$_{200}$)═, provided a) that at least one of Z1, Z3, and Z5 is —N═;

b) that no more than two of Z1, Z2, Z3, Z4, and Z5 are —N═;

c) that no more than three of Z1, Z3, Z4, Z5, and Z6 are other than —N═ or —C(H)═;

d) when Z4 or Z6 is —C(R$_{100}$)═, that (i) one of Z1 and Z3 is —C(R$_{100}$)═, (ii) Z5 is —C(R$_{200}$)═, or (iii) both Z4 and Z6 are —C(R$_{100}$)═;

Each $R^{100}$ is independently is —(C1-C4)aliphatic)$_p$-Y2;

Y2 is halo, —CN, —NO$_2$, —CF$_3$, —OCF$_3$, —SR$_{600}$, —S(O)R$_{600}$, —SO$_2$R$_{600}$, —SO$_2$NR$_{600}$, —COOR$_{600}$, —C(O)N(R$_{600}$)$_2$, or —OR$_{600}$; or Each $R_{200}$ is independently $R_{100}$ or phenyl optionally substituted with 1-3 halo, —CN, —NO$_2$, —CF$_3$, —OCF$_3$, —OH;

Each $R^{400}$ is independently OR$^5$, OR$^6$, S(O)R$^6$, S(O)R$^5$, SO$_2$R$^6$, SO$_2$R$^5$, SO$_2$N(R$^6$)$_2$, SO$_2$N(R$^5$)$_2$, SO$_2$NR$^5$R$^6$, SO$_3$R$^6$, SO$_3$R$^5$, C(O)R$^5$, C(O)OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^6$, C(O)N(OR$^5$) R$^6$, C(O)N(OR$^6$)R$^5$, C(O)N(OR$^5$)R$^5$, C(NOR$^6$)R$^6$, C(NOR$^6$) R$^5$, C(NOR$^5$)R$^6$, and C(NOR$^5$)R$^5$;

Each $R_{600}$ is independently H or aliphatic optionally substituted with 1-3 substituents selected from halo, —CN, —NO$_2$, —CF$_3$, —OCF$_3$, or —OH;

Each x is independently 1 or 2;

Each i is 0, 1 2, or 3;

Each m is independently 1 or 2; and

Each p is independently 0 or 1;

Each w is independently 0 or 1;

further provided that (1) when G is N and $A_{IV}$ is bicyclo[2.2.1]hept-5-en-2-yl-carbonyl, then V is not 2-(phenyl)-6-acetamidoethyl-amino-pyrimidin-4-yl or 2-(4-chlorophenyl)-6-acetamidoethyl-amino-pyrimidin-4-yl;

(2) the compound is not 2-(4-bicyclo[2.2.1]hept-2-yl-1-piperazinyl)-pyrimidine or 2-[4-(bicyclo[2.2.1]hept-5-en-2-ylmethyl)-1-piperazinyl]-pyrimidine; and (3) when G is N and $A_{IV}$ is azabicyclo[3.2.1]octane-8-carboxylic acid t-butyl ester, then V is not 5-cyano-4-[(2,4-difluorophenyl)methyl]amino-2-pyrimidinyl, 5-ethoxycarbonyl-2-pyrimidinyl, or pyridine-2-yl-5-carboxylic acid.

III. Specific Embodiments

Ring A, $A_{II}$, and $A_{IV}$

Ring A is used interchangeably with Ring $A_{II}$ and Ring $A_{IV}$. According to one embodiment, A is selected from:

(ia)

[bicyclic structure with W₁]

(ib)

[bicyclic structure with W₁]

-continued

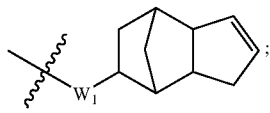
(ic)

wherein W₁ is as defined above.

According to another embodiment, A is (ia). Or, A is (ib). Or, A is (ic).

According to one embodiment, x is 1. Or, x is 2.

According to another embodiment, W₁ is a bond or $CH_2$.

According to another embodiment, A is selected from:

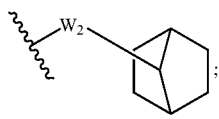
(iia)

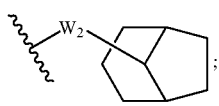
(iib)

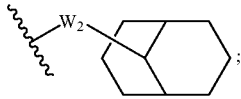
(iic)

wherein W₂ is as defined above.

According to one embodiment, A is selected from (iia), (iib), or (iic). Or, A is (iia). Or, A is (iib). Or, A is (iic).

According to one embodiment, W₂ is a bond or $CH_2$.

According to one embodiment, A is selected from:

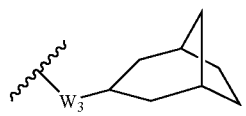
iiia

iiib

iiic wherein W₃ is as defined above.

According to one embodiment, A is (iiia). Or, A is (iiib). Or, A is (iiic).

According to one embodiment, W₃ is a bond or $CH_2$.

According to another embodiment, A is selected from:

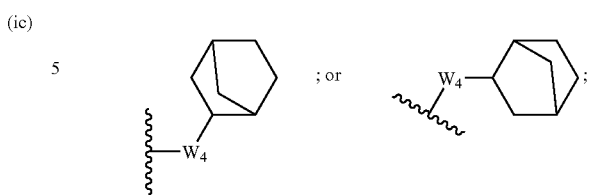

wherein W₄ is as defined above.

According to another embodiment, A is selected from:

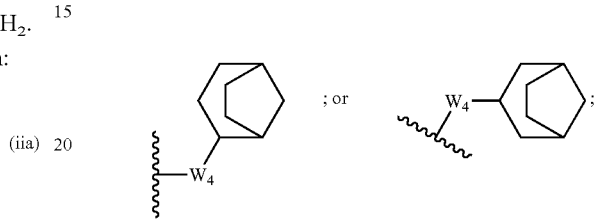

wherein W₄ is as defined above.

According to one embodiment, A is (iva). According to another embodiment, A is (ivb).

According to one embodiment, W₄ is a bond or $CH_2$.

According to another embodiment, A is adamantyl or adamantylmethyl.

According to another embodiment, A is

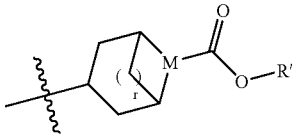

wherein r, M and R' are defined above in formula III. In one aspect of this embodiment, r is 0. In another aspect of this embodiment, r is 1. In still another aspect of this embodiment, r is 2. M is CH. M is N. R' is aliphatic. R' is alkyl. R' is methyl, ethyl, n-propyl, n-butyl, t-butyl, or isopropyl.

According to another embodiment, (i) when G is N and V is pyrimidin-2-yl, then A is not bicyclo[2.2.1]hept-2-yl or bicyclo[2.2.1]hept-5-en-2-yl; or (ii) when G is N and A is bicyclo[2.2.1]hept-5-en-2-yl-carbonyl, then V is not 2-(phenyl)-6-acetamidoethyl-amino-pyrimidin-4-yl or 2-(4-chlorophenyl)-6-acetamidoethyl-amino-pyrimidin-4-yl.

Ring V in Formulae I, II, and IV and Ring E in Formula III

According to a preferred embodiment, ring V is a six-membered aromatic ring containing 1-3 nitrogen ring atoms. According to one embodiment, ring V is a six-membered aromatic ring containing 1 nitrogen ring atom. According to another embodiment, ring V is a six-membered aromatic ring containing 2 nitrogen ring atoms. According to another embodiment, V is a 5-6 membered unsaturated, monocyclic, heterocyclic ring containing 1-4 ring heteroatoms selected from O, S, and N.

According to one embodiment, ring V or ring E is selected from optionally substituted:

(a) 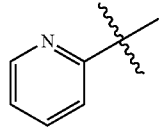

(b) 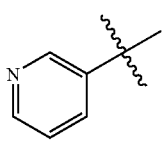

(c) 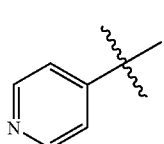

(d) 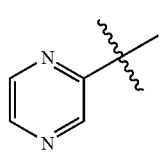

(e) 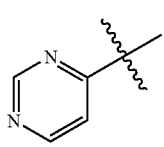

(f) 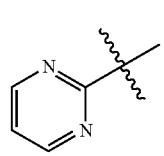

(g) 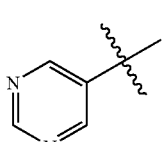

(h) 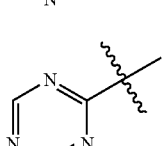

(i) 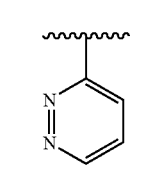

(j) 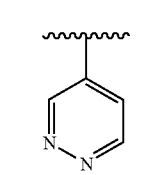

(k) 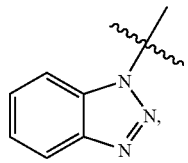

In one aspect of this embodiment, each of the c-ring systems (a) through (k) is optionally substituted with 1 to 3 substituents selected from $R^1$, $R^2$, $R^3$, $R^4$, or $R^5$.

According to another embodiment, ring V or ring E is

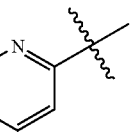

wherein ring E is optionally substituted with up to four substituents independently selected from $R^1$, $R^2$, $R^3$, $R^4$, or $R^5$.

According to another embodiment, ring V or ring E is (a) 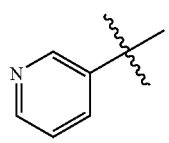

(b) 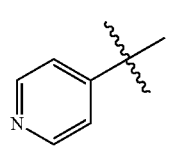

(c) 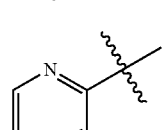

(d) 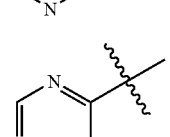

(e) 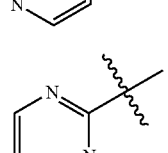

(f)

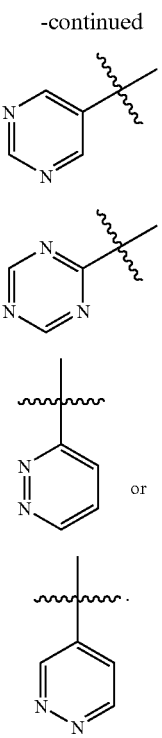

According to another embodiment, ring V or ring E is an optionally substituted pyridyl or pyrazinyl. Preferred substituents on ring V or ring E include halo, cyano, C1-C4 alkyl, or CF$_3$. More preferably, ring V or ring E is 3-cyano-2-pyridyl or 5-cyano-2-pyridyl.

According to another embodiment, ring V or ring E is contains up to 3 R$^1$ substituents, wherein each R$^1$ is independently as defined above. Or, ring V or ring E contains 1 or 2 R$^1$ substituents, wherein each R$^1$ is independently as defined herein. Ring V or ring E contains 1 to 3 of halo, cyano, C1-C4 alkyl, or CF$_3$.

Substituents R1, R2, R3, R4, R5, R6, and R7

According to another preferred embodiment, R$^1$ is R$^6$, wherein R$^6$ is straight chain or branched (C1-C6)alkyl or (C2-C6 alkenyl) or alkynyl, optionally substituted with R$^7$.

According to another preferred embodiment, R$^1$ is (CH$_2$)$_m$—Y, wherein m is 0, 1, or 2, and Y is halo, CN, NO$_2$, CF$_3$, OCF$_3$, OH, SR$^6$, S(O)R$^6$, SO$_2$R$^6$, COOH, COOR$^6$ or OR$^6$.

According to another preferred embodiment, R$^1$ is selected from halo, CF$_3$, CN, NH$_2$, NH(C1-C4 alkyl), NHC(O)CH$_3$, OH, O(C1-C4 alkyl), OPh, O-benzyl, S—(C1-C4 alkyl), C1-C4 aliphatic, NO$_2$, CN, methylenedioxy, ethylenedixoy, SO$_2$NH(C1-C4 alkyl), or SO$_2$N(C1-C4 alkyl)$_2$.

According to another more preferred embodiment, R$^1$ is selected from methyl, n-propyl, i-propyl, t-butyl. Or, R$^1$ is selected from CN, halo, NO2, CF$_3$, OCF$_3$, or OH, preferably CN. Or, R$^1$ is selected from NH(CH$_3$), NHC(O)CH$_3$, OCH$_3$, OPh, O-benzyl, S—(C$_2$H$_5$), S—CH$_3$-methylenedioxy, SO$_2$NH(n-propyl), or SO$_2$N(n-propyl)$_2$. Or, R$^1$ is selected from NHC(O)CH$_3$, OCH$_3$, OPh, O-benzyl, S—(C$_2$H$_5$), S—CH$_3$-methylenedioxy, SO$_2$NH(n-propyl), or SO$_2$N(n-propyl)$_2$.

According to a preferred embodiment, R$^2$ is a straight chain or branched (C1-C6)alkyl or (C2-C6) alkenyl or alkynyl, optionally substituted with R$^1$, R$^4$, or R$^5$. More preferably, R$^2$ is a straight chain or branched (C1-C4)alkyl or (C2-C4) alkenyl or alkynyl, optionally substituted with R$^1$, R$^4$, or R$^5$.

According to a preferred embodiment, R$^3$ is optionally substituted phenyl, napthyl, C5-C10 heteroaryl or C3-C7 heterocyclyl. More preferably, R$^3$ is an optionally substituted phenyl, C5-C6 heteroaryl, or C3-C6 heterocyclyl.

According to a preferred embodiment, R$^4$ is selected from OR$^5$ or OR$^6$.

According to a preferred embodiment, R$^5$ is C5-C6 cycloalkyl, C6 or C10C aryl, C5-C10 heteroaryl or C3-C7 heterocyclyl, optionally substituted with up to 2 R$^1$. More preferably, R$^5$ is an optionally substituted cyclohexyl, phenyl, C5-C6 heteroaryl, or C3-C6 heterocyclyl.

According to a preferred embodiment, R$^6$ is H.

According to another preferred embodiment, R$^6$ is a straight chain or branched (C1-C6)alkyl or (C2-C6 alkenyl) or alkynyl, optionally substituted with R$^7$.

According to another preferred embodiment, R$^6$ is a straight chain or branched (C1-C6)alkyl or (C2-C6 alkenyl) or alkynyl.

According to a preferred embodiment, R$^7$ is C5-C6 cycloalkyl, phenyl, naphthyl, C5-C10 heteroaryl or C3-C7 heterocyclyl, optionally substituted with straight chain or branched (C1-C6)alkyl or (C2-C6 alkenyl) or alkynyl. Or, R$^7$ is C5-C6 cycloalkyl, phenyl, naphthyl, C5-C10 heteroaryl or C3-C7 heterocyclyl, optionally substituted with 1-2-methylenedioxy, 1,2-ethylenedioxy, or (CH$_2$)$_n$—Z. More preferably, R$^7$ is an optionally substituted cyclohexyl, phenyl, C5-C6 heteroaryl, or C3-C6 heterocyclyl.

Basic Nitrogen Atoms

In some embodiments, the compounds of formulae I and II do hot include any additional basic nitrogen atoms other than those contained within the V-ring, E ring, A ring, or the piperazine/piperidine ring. For example, the substituents, if any, on the V-ring, E ring, A-ring or the piperazine/piperidine ring do not include any basic nitrogen atoms, wherein a basic nitrogen atom is defined as any nitrogen whose conjugate acid pka is greater than 7.1. For instance, the nitrogen atom at the 4 position relative to V is a basic nitrogen atom. In other embodiments, A and substituents attached to A do not include any basic nitrogen atoms, but V along with substituents attached to V may include one or more basic nitrogen atoms. Alternatively, ring A does not include any basic nitrogen atoms that form ring A, such as the nitrogen in piperidine, but V and substituents attached to V and A may include one or more basic nitrogen atoms.

Specific Embodiments

Specific embodiments of compounds useful for modulating muscarininc receptors includes all combinations of the generic descriptions, specific aspects, and embodiments described above.

According to a preferred embodiment, the specific compounds of formulae (I, II, III, or IV) are selected from Table 1 below:

TABLE 1

1. 1-(5-bicyclo[2.2.1]hept-2-enylmethyl)-4-(3-nitro-2-pyridyl)-piperazine
2. 2-[4-(2-adamantyl)piperazin-1-yl]nicotinonitrile
3. 2-(4-norbornan-2-ylpiperazin-1-yl)-6-(trifluoromethyl)nicotinonitrile
4. 2-[1-(5-bicyclo[2.2.1]hept-2-enylmethyl)-4-piperidyl]-4,6-dimethoxy-pyrimidine
5. 1-(3-nitro-2-pyridyl)-4-norbornan-2-yl-piperazine
6. 2-[4-(5-bicyclo[2.2.1]hept-2-enylmethyl)piperazin-1-yl]nicotinamide
7. 1-(3-chloro-2-pyridyl)-4-norbornan-2-yl-piperazine
8. 2-[4-(norbornan-2-ylmethyl)piperazin-1-yl]-6-(trifluoromethyl)nicotinonitrile
9. 1-[1-(3-bicyclo[3.2.1]octyl)-4-piperidyl]-1H-benzotriazole
10. 2-(4-norbornan-2-ylpiperazin-1-yl)nicotinamide
11. 3-[4-(4-cyano-6-phenyl-pyridazin-3-yl)piperazin-1-yl]-8-azabicyclo[3.2.1]octane-8-carboxylic acid ethyl ester
12. 3-[4-(3-cyano-2-pyridyl)piperazin-1-yl]-8-azabicyclo[3.2.1]octane-8-carboxylic acid ethyl ester
13. 6-[4-(5-bicyclo[2.2.1]hept-2-enylmethyl)piperazin-1-yl]nicotinonitrile
14. 6-[4-(norbornan-2-ylmethyl)piperazin-1-yl]nicotinamide
15. 1-(5-bicyclo[2.2.1]hept-2-enylmethyl)-4-(6-methyl-2-pyridyl)-piperazine
16. 3-[4-(5-bicyclo[2.2.1]hept-2-enylmethyl)piperazin-1-yl]-2,5-dimethyl-pyrazine
17. 2-[4-(5-bicyclo[2.2.1]hept-2-enylmethyl)piperazin-1-yl]-3-methyl-pyrazine
18. 1-norbornan-2-yl-4-(4-pyridyl)piperazine
19. 6-(4-norbornan-2-ylpiperazin-1-yl)nicotinonitrile
20. 2-[4-(5-bicyclo[2.2.1]hept-2-enylmethyl)piperazin-1-yl]-3-methyl-pyridine
21. 1-(5-bicyclo[2.2.1]hept-2-enylmethyl)-4-(6-chloro-2-pyridyl)-piperazine
22. 5-ethyl-2-[4-(norbornan-2-ylmethyl)piperazin-1-yl]-pyrimidine
23. 3-[4-(4-bicyclo[3.2.1]octylmethyl)piperazin-1-yl]pyrazine-2-carbonitrile
24. 3-[4-[3-cyano-6-(trifluoromethyl)-2-pyridyl]piperazin-1-yl]-8-azabicyclo[3.2.1]octane-8-carboxylic acid ethyl ester
25. 3-[4-(4-pyridyl)piperazin-1-yl]-8-azabicyclo[3.2.1]octane-8-carboxylic acid ethyl ester
26. 1-(5-bicyclo[2.2.1]hept-2-enylmethyl)-4-(3,5-dichloro-4-pyridyl)-piperazine
27. 2-[4-(3-bicyclo[3.2.1]octyl)piperazin-1-yl]nicotinonitrile
28. 3-[4-[5-(trifluoromethyl)-2-pyridyl]piperazin-1-yl]-8-azabicyclo[3.2.1]octane-8-carboxylic acid ethyl ester
29. 3-[4-(1H-benzotriazol-1-yl)-1-piperidyl]-8-azabicyclo[3.2.1]octane-8-carboxylic acid ethyl ester
30. 3-[4-(3-fluoro-2-pyridyl)piperazin-1-yl]-8-azabicyclo[3.2.1]octane-8-carboxylic acid ethyl ester
31. 6-methyl-2-(4-norbornan-2-ylpiperazin-1-yl)-nicotinonitrile
32. 2-(4-norbornan-2-ylpiperazin-1-yl)nicotinonitrile
33. 3-[4-(3-cyano-5-phenyl-2-pyridyl)piperazin-1-yl]-8-azabicyclo[3.2.1]octane-8-carboxylic acid ethyl ester
34. 6-[4-(5-bicyclo[2.2.1]hept-2-enylmethyl)piperazin-1-yl]nicotinonitrile
35. 1-(3-bicyclo[3.2.1]octyl)-4-(4-pyridyl)piperazine
36. 3-[4-(5-carbamoyl-2-pyridyl)piperazin-1-yl]-8-azabicyclo[3.2.1]octane-8-carboxylic acid ethyl ester
37. 1-[1-(5-bicyclo[2.2.1]hept-2-enylmethyl)-4-piperidyl]-1H-benzotriazole
38. 3-[[4-(3-cyanopyrazin-2-yl)piperazin-1-yl]methyl]-8-azabicyclo[3.2.1]octane-8-carboxylic acid ethyl ester
39. 2-[4-(5-bicyclo[2.2.1]hept-2-enylmethyl)piperazin-1-yl]pyrazine
40. 2,5-dimethyl-3-(4-norbornan-2-ylpiperazin-1-yl)-pyrazine
41. 1-(5-bicyclo[2.2.1]hept-2-enylmethyl)-4-(4-pyridyl)piperazine
42. 2-[4-(5-bicyclo[2.2.1]hept-2-enylmethyl)piperazin-1-yl]nicotinonitrile
43. 3-(4-norbornan-2-ylpiperazin-1-yl)pyrazine-2-carbonitrile
44. 2-(4-norbornan-2-ylpiperazin-1-yl)pyrazine
45. 3-[4-(3-cyanopyrazin-2-yl)piperazin-1-yl]-8-azabicyclo[3.2.1]octane-8-carboxylic acid ethyl ester
46. 2-[4-(norbornan-2-ylmethyl)piperazin-1-yl]-5-phenyl-nicotinonitrile
47. 1-(5-bicyclo[2.2.1]hept-2-enylmethyl)-4-[5-(trifluoromethyl)-2-pyridyl]-piperazine
48. 1-(5-bicyclo[2.2.1]hept-2-enylmethyl)-4-(2-pyridyl)piperazine
49. 3-[4-(3-sulfamoyl-4-pyridyl)piperazin-1-yl]-8-azabicyclo[3.2.1]octane-8-carboxylic acid ethyl ester
50. 1-(1-norbornan-2-yl-4-piperidyl)-1H-benzotriazole
51. 3-[4-(5-acetyl-2-pyridyl)piperazin-1-yl]-8-azabicyclo[3.2.1]octane-8-carboxylic acid ethyl ester
52. 1-(5-bicyclo[2.2.1]hept-2-enylmethyl)-4-(3-chloro-2-pyridyl)-piperazine
53. 2-[4-(5-bicyclo[2.2.1]hept-2-enylmethyl)piperazin-1-yl]-6-(trifluoromethyl)nicotinonitrile
54. 2-[1-(5-bicyclo[2.2.1]hept-2-enylmethyl)-4-piperidyl]nicotinonitrile
55. 4-[4-(norbornan-2-ylmethyl)piperazin-1-yl]pyridine-3-sulfonamide
56. 3-[4-(4-cyano-2-pyridyl)piperazin-1-yl]-8-azabicyclo[3.2.1]octane-8-carboxylic acid ethyl ester
57. 3-[4-(4,6-dimethoxypyrimidin-2-yl)-1-piperidyl]-8-azabicyclo[3.2.1]octane-8-carboxylic acid ethyl ester
58. 3-[4-[6-chloro-3-cyano-4-(trifluoromethyl)-2-pyridyl]piperazin-1-yl]-8-azabicyclo[3.2.1]octane-8-carboxylic acid ethyl ester
59. 3-[4-(norbornan-2-ylmethyl)piperazin-1-yl]-6-phenyl-pyridazine-4-carbonitrile
60. 1-(3-methyl-2-pyridyl)-4-norbornan-2-yl-piperazine
61. 1-(2-bicyclo[3.2.1]octyl)-4-(4-pyridyl)piperazine
62. 2-[4-(5-bicyclo[2.2.1]hept-2-enylmethyl)piperazin-1-yl]-6-methyl-nicotinonitrile

TABLE 1-continued 63 2-methyl-3-(4-norbornan-2-ylpiperazin-1-yl)-pyrazine
64 2-[4-(4-bicyclo[3.2.1]octylmethyl)piperazin-1-yl]nicotinonitrile
65 1-norbornan-2-yl-4-(2-pyridyl)piperazine
66 3-[4-(5-cyano-2-pyridyl)piperazin-1-yl]-8-azabicyclo[3.2.1]octane-8-carboxylic acid ethyl ester
67 3-[4-(5-ethylpyrimidin-2-yl)piperazin-1-yl]-8-azabicyclo[3.2.1]octane-8-carboxylic acid ethyl ester
68 3-[[4-(3-cyano-2-pyridyl)piperazin-1-yl]methyl]-8-azabicyclo[3.2.1]octane-8-carboxylic acid ethyl ester
69 1-(5-bicyclo[2.2.1]hept-2-enylmethyl)-4-[3-(trifluoromethyl)-2-pyridyl]-piperazine
70 3-[4-(5-bicyclo[2.2.1]hept-2-enylmethyl)piperazin-1-yl]pyrazine-2-carbonitrile
71 2-(4-norbornan-2-ylpiperazin-1-yl)pyrimidine
72 4,6-dimethyl-2-(4-norbornan-2-ylpiperazin-1-yl)-pyrimidine
73 6-methyl-2-[4-(norbornan-2-ylmethyl)piperazin-1-yl]-5-phenyl-nicotinonitrile
74 1-(5-bicyclo[2.2.1]hept-2-enylmethyl)-4-[3-chloro-5-(trifluoromethyl)-2-pyridyl]-piperazine
75 1-(2-adamantyl)-4-(4-pyridyl)piperazine
76 2-[4-(5-bicyclo[2.2.1]hept-2-enylmethyl)piperazin-1-yl]pyrimidine
77 1-(6-methyl-2-pyridyl)-4-norbornan-2-yl-piperazine
78 3-[4-(3-cyano-4,6-dimethyl-2-pyridyl)piperazin-1-yl]-8-azabicyclo[3.2.1]octane-8-carboxylic acid ethyl ester

IV. Synthetic Schemes

The compounds of formulae (I, II, III, and IV) may be readily synthesized using methods known in the art. An exemplary synthetic route to produce compounds of formulae (I, II, III, and IV) is provided below in Scheme 1.

Scheme 1:

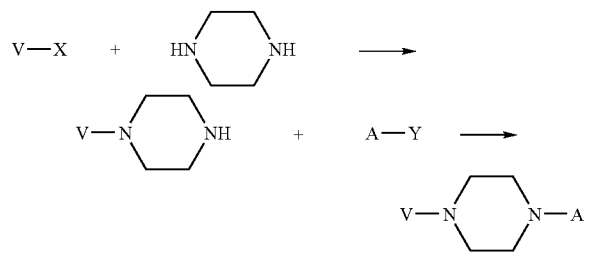

Referring to Scheme 1, the reaction of piperazine with a ring V compound bearing a suitable leaving group X, optionally in the presence of a coupling catalyst, produces an intermediate that upon reaction with A-Y, wherein Y is a suitable functionality, in the presence of a suitable reducing agent using, produces compounds of formula (I).

Examples of X include halogen, tosylate, mesylate and triflate. Examples of a suitable functionality Y include an aldehyde or a ketone. An example of a suitable reducing agent includes sodium triacetoxyborohydride. An non-limiting example of a coupling catalyst is acetato(2'-di-t-butylphosphino-1,1'-biphenyl-2-yl)palladium (II).

The synthetic route depicted above is generic and can be readily adapted for other embodiments of compound formulae (I, II, III, and IV). It will also be recognized that variations of Scheme I, for example introducing Ring A before Ring V (or Ring E) and conducting each attachment with the same or different chemistry for each step, also constitute suitable methods for the preparation of compounds of Formulae (I, II, III, and IV).

V. Formulations, Administrations, and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, II, III, and IV) are selective modulators of $M_1$, $M_2$ and $M_4$. More preferably, the compounds of formulae (I, II, III, and IV) are selective modulators of $M_1$ and/or $M_4$. Yet more preferably, the compounds of formulae (I, II, III, and IV) are selective modulators of one of $M_1$. Or, preferably, the compounds of formulae (I, II, III, and IV) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e, an agonist) or inhibits the activity of a muscarinic receptor.

According to a preferred embodiment, the compounds of formula (I) are selective activators of $M_1$, $M_2$ and $M_4$. More preferably, these compounds are selective activators of $M_1$ and/or $M_4$. Yet more preferably, the compounds of formula (I) are selective activators of $M_1$. Or, preferably, the compounds of formula (I) are selective activators of $M_4$.

According to another embodiment, the compounds of formula (II) are selective inhibitors of one or more of $M_1$, $M_2$, or $M_4$. Preferably, the compounds of formula (II) are selective inhibitors of $M_1$. Or, the compounds of formula (II) are selective inhibitors of $M_4$.

According to another embodiment, the compounds of formula (III) are selective inhibitors of one or more of $M_1$, $M_2$, or $M_4$. Preferably, the compounds of formula (III) are selective inhibitors of $M_1$. Or, the compounds of formula (III) are selective inhibitors of $M_4$.

According to another embodiment, the compounds of formula (IV) are selective inhibitors of one or more of $M_1$, $M_2$, or M4. Preferably, the compounds of formula (IV) are selective inhibitors of $M_1$. Or, the compounds of formula (IV) are selective inhibitors of $M_4$.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, comprising the step of administering to said mammal a composition comprising a compound of formula (I), or a preferred embodiment thereof as set forth above.

According to a preferred embodiment, the present invention provides a method of treating a disease mediated by a muscarinic receptor comprising the step of administering to said mammal a composition comprising a compound of formula (I), or a preferred embodiment thereof as set forth above. Preferably, said disease is mediated by $M_1$. Or, said disease is mediated by $M_4$.

According to a preferred embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradhycardia, gastric acid secretion, asthma, or GI disturbances.

According to a preferred embodiment, the present invention is useful for treating or reducing the severity of psychosis, Alzheimer's disease, pain, or Parkinson's disease.

In order that the invention described herein may be more fully understood, the following examples are set forth. It should be understood that these examples are for illustrative purposes only and are not to be construed as limiting this invention in any manner.

All references cited above are incorporated herein by reference.

EXAMPLES

Example 1

Synthesis of 2-(4-Bicyclo[2.2.1]hept-2-yl-piperazin-1-yl)-6-trifluoromethyl-nicotinamide

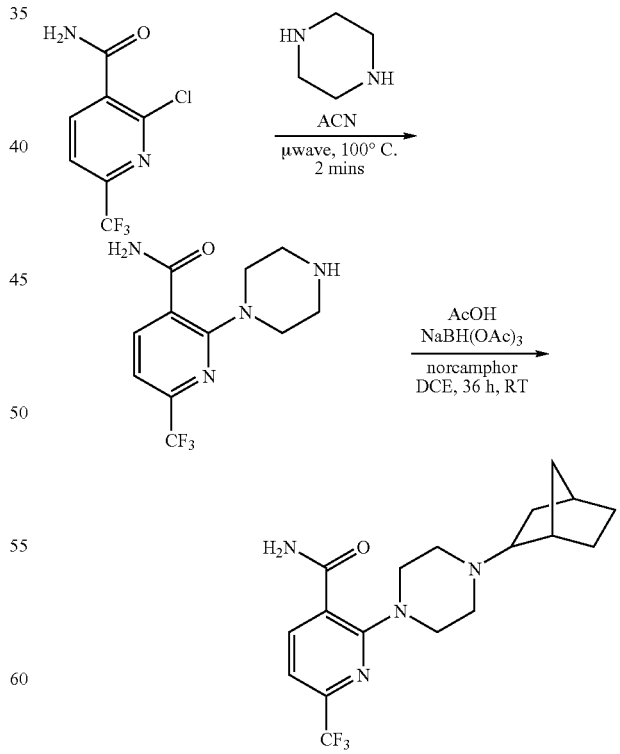

449 mg (2.00 mmol, 1.0 eq) 2-Chloro-6-trifluoromethyl nicotinamide, 344 mg (4.00 mmol, 2.0 eq) piperazine and 2.0 mL anhydrous acetonitrile (ACN) were combined in a microwave vial and microwaved at 100° C. for 2 minutes. The reaction was diluted with 2.0 mL methanol and centrifuged (4,000 rpm, RT, 8 mins). The supernatant was filtered and purified by reverse-phase HPLC (1-25% CH$_3$CN in 0.085% TFA (aq), 50 mL/min, 2×2.0 mL injected). The appropriate fractions were concentrated under reduced pressure. The resulting solids were dissolved in 5.0 mL 1.0 N sodium hydroxide and extracted with ethyl acetate (3×20 mL). The organic layers were combined, washed with brine, dried (Na$_2$SO$_4$) and concentrated under reduced pressure.

Yield=281 mg (51%) as off-white needles (isolated as the free base); Purity=99+%; $^1$H-NMR (400 MHz, DMSO-d$_6$) δ 8.00 (br s, 1H), 7.83 (d, J=7.5 Hz, 1H), 7.69 (br s, 1H), 7.2 (d, J=7.6 Hz, 1H), 3.35 (br m, 4H), 2.79 (br m, 4H), 2.38 (br s, 1H); LC/MS retention time (10-99% CH$_3$CN/0.085% TFA gradient over 5 min): 1.15 min; Theoretical (M+H)$^+$ m/z for C$_{11}$H$_{13}$F$_3$N$_4$O=275.1; Found 275.0.

55 mg (0.20 mmol, 1.0 eq) of 2-piperazin-1-yl-6-trifluoromethyl-nicotinamide was suspended in 5.0 mL anhydrous 1,2-dichloroethane and treated with 1.0 eq (22 mg) norcamphor. 2.0 eq (24 mg) glacial acetic acid was then added, followed by 2.8 eq (119 mg) sodium triacetoxyborohydride. The reaction vial was flushed with nitrogen and stirred at room temperature for 36 hours. The reaction mixture was concentrated under reduced pressure and the resulting residue dissolved in 2.0 mL DMSO:methanol (1:1). The solution was filtered and purified by reverse-phase HPLC (2-99% CH$_3$CN in 0.085% TFA (aq), 50 mL/min, 2.0 mL injected). Yield=34 mg (35%) (isolated as the mono-TFA salt); Purity=99%; $^1$H-NMR (400 MHz, DMSO-d$_6$) δ 9.32 (br s, 1H), 8.13 (s, 1H), 7.98 (d, J=7.5 Hz, 1H), 7.82 (s, 1H), 7.41 (d, J=7.6 Hz, 1H), 4.00 (m, 2H), 3.58 (br m, 3H), 3.41 (br m, 2H), 3.15 (br m, 2H), 2.62 (br s, 1H), 2.33 (br s, 1H), 2.02 (m, 1H), 1.59 (br m, 3H), 1.42 (m, 3H), 1.22 (m, 1H); LC/MS retention time (10-99% CH$_3$CN/0.085% TFA gradient over 5 min): 1.91 min; Theoretical (M+H)$^+$ m/z for C$_{18}$H$_{23}$F$_3$N$_4$O=369.2; Found 369.0.

Example 2

Synthesis of 1-Bicyclo[2.2.1]hept-5-en-2-ylmethyl-4-(2-methoxy-5-trifluoromethyl-pyridin-3-yl)-piperazine

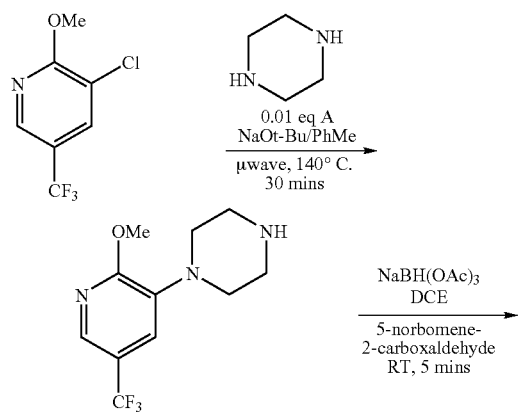

-continued

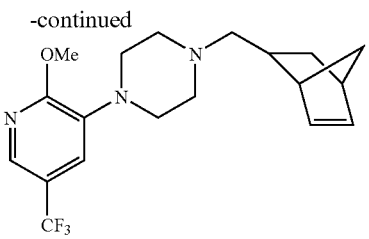

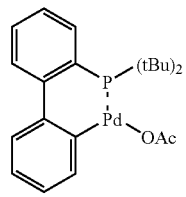

2.5 mg (0.0050 mmol, 0.010 eq) Acetato(2'-di-t-butylphosphino-1,1'-biphenyl-2-yl)palladium (II) (A), 67 mg (0.70 mmol, 1.4 eq) NaOt-Bu and 1.0 mL anhydrous toluene were combined in a microwave vial. 106 mg (0.50 mmol, 1.0 eq) 3-Chloro-2-methoxy-5-trifluoromethylpyridine was added, followed by 129 mg (1.5 mmol, 3.0 eq) piperazine. The vial was flushed with nitrogen prior to being microwaved at 140° C. for 30 minutes. The reaction mixture was diluted with 1.0 mL DMSO:methanol (1:1), filtered and purified by reverse-phase HPLC (2-99% CH$_3$CN in 0.085% TFA (aq), 50 mL/min, 2.0 mL injected). Yield=85 mg (45%) (isolated as the mono-TFA salt); Purity=99%; $^1$H-NMR (400 MHz, DMSO-d$_6$) δ 8.99 (br s, 2H), 8.24 (d, J=2.0 Hz, 1H), 7.51 (d, J=2.1 Hz, 1H), 4.02 (s, 3H), 3.32 (br m, 8H); LC/MS retention time (10-99% CH$_3$CN/0.085% TFA gradient over 5 min): 1.73 min; Theoretical (M+H)$^+$ m/z for C$_{11}$H$_{14}$F$_3$N$_3$O=262.1; Found 262.0.

75 mg (0.20 mmol, 1.0 eq) of 1-(2-methoxy-5-trifluoromethyl-pyridin-3-yl)-piperazine (as the mono-TFA salt) was suspended in 1.0 mL anhydrous 1,2-dichloroethane and treated with 1.0 eq (20 mg) triethylamine. 1.0 eq (24 mg) 5-Norbornene-2-carboxaldehyde was added, followed by 1.4 eq (59 mg) sodium triacetoxyborohydride. The reaction was stirred at room temperature for 5 minutes, then quenched with 1.0 mL DMSO:methanol (1:1). The reaction mixture was filtered and purified by reverse-phase HPLC (2-99% CH$_3$CN in 0.085% TFA (aq), 50 mL/min, 2.0 mL injected). Yield=23 mg (24%) (isolated as the mono-TFA salt); Purity=99%; $^1$H-NMR (400 MHz, DMSO-d$_6$) δ 10.08 (br s, 1H), 8.25 (d, J=1.9 Hz, 1H), 7.50 (d, J=2.2 Hz, 1H), 6.28 (m, 0.8H), 6.18 (m, 0.4H), 6.07 (m, 0.8H), 4.02 (s, 3H), 3.71 (br m, 4H), 2.81-3.26 (m, 8H), 2.54 (m, 1H), 2.03 (m, 0.8H), 1.80 (m, 0.2H), 1.30-1.41 (m, 2.5H), 0.71 (m, 0.8H); LC/MS retention time (10-99% CH$_3$CN/0.085% TFA gradient over 5 min): 2.30 min; Theoretical (M+H)$^+$ m/z for C$_{19}$H$_{24}$F$_3$N$_3$O=368.2; Found 368.2.

Example 3

Synthesis of 4-Bicyclo[2.2.1]hept-5-en-2-ylmethyl-3,4,5,6-tetrahydro-2H-[1,2']bipyrazinyl-3'-carbonitrile

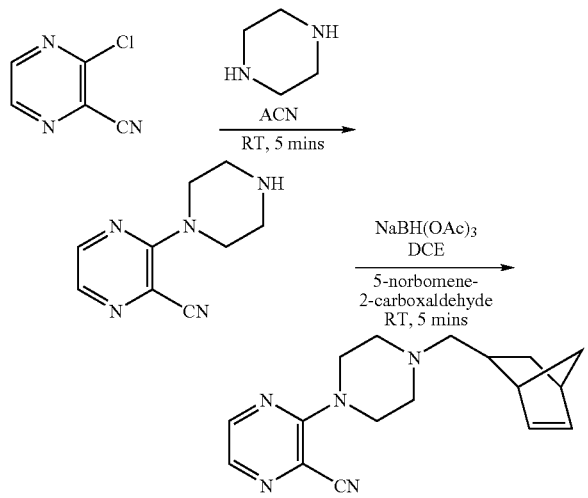

70 mg (0.50 mmol, 1.0 eq) 3-Chloropyrazine-2-carbonitrile and 86 mg (1.0 mmol, 2.0 eq) piperazine were added to 1.0 mL anhydrous acetonitrile and stirred at room temperature for 5 minutes. The reaction was diluted with 1.0 mL methanol, filtered and purified by reverse-phase HPLC (1-25% $CH_3CN$ in 0.085% TFA (aq), 50 mL/min, 2.0 mL injected). Yield=63 mg (42%) (isolated as the mono-TFA salt); Purity=99%; $^1$H-NMR (400 MHz, DMSO-$d_6$) δ 9.15 (br s, 2H), 8.56 (d, J=2.3 Hz, 1H), 8.27 (d, J=2.3 Hz, 1H), 3.94 (br m, 4H), 3.31 (br m, 4H); LC/MS retention time (10-99% $CH_3CN$/0.085% TFA gradient over 5 min): 0.41 min; Theoretical (M+H)$^+$ m/z for $C_9H_{11}N_5$=190.1; Found 190.1.

61 mg (0.20 mmol, 1.0 eq) of 3,4,5,6-Tetrahydro-2H-[1,2'] bipyrazinyl-3'-carbonitrile (as the mono-TFA salt) was suspended in 1.0 mL anhydrous 1,2-dichloroethane and treated with 1.0 eq (20 mg) triethylamine. 1.0 eq (24 mg) 5-Norbornene-2-carboxaldehyde was added, followed by 1.4 eq (59 mg) sodium triacetoxyborohydride. The reaction was stirred at room temperature for 5 minutes, then quenched with 1.0 mL DMSO:methanol (1:1). The reaction mixture was filtered and purified by reverse-phase HPLC (2-99% $CH_3CN$ in 0.085% TFA (aq), 50 mL/min, 2.0 mL injected). Yield=40 mg (49%) (isolated as the mono-TFA salt); Purity=99+%; $^1$H-NMR (400 MHz, DMSO-$d_6$) δ 10.20 (br s, 1H), 8.57 (d, J=2.3 Hz, 1H), 8.29 (d, J=2.2 Hz, 1H), 6.28 (m, 0.8H), 6.18 (m, 0.4H), 6.05 (m, 0.8H), 4.47 (m, 2H), 3.55 and 3.71 (2 br m, 4H), 3.31 (m, 1H), 2.86-3.01 (br m, 4H), 2.54 (m, 1H), 2.02 (m, 0.8H), 1.80 (m, 0.2H), 1.30-1.41 (m, 3H), 0.68 (m, 0.8H); LC/MS retention time (10-99% $CH_3CN$/0.085% TFA gradient over 5 min): 1.77 min; Theoretical (M+H)$^+$ m/z for $C_{17}H_{21}N_5$=296.2; Found 296.2.

Example 4

Additional compounds listed in Table 2 were produced via known methodologies and synthetic procedures and those described herein.

TABLE 2

| No. | Name | LCMS Plus | LCMS RT |
|---|---|---|---|
| 1 | 1-(5-bicyclo[2.2.1]hept-2-enylmethyl)-4-(3-nitro-2-pyridyl)-piperazine | 315 | 1.98 |
| 2 | 2-[4-(2-adamantyl)piperazin-1-yl]nicotinonitrile | 323.2 | 2.01 |
| 3 | 2-(4-norbornan-2-ylpiperazin-1-yl)-6-(trifluoromethyl)nicotinonitrile | 351.2 | 2.17 |
| 4 | 2-[1-(5-bicyclo[2.2.1]hept-2-enylmethyl)-4-piperidyl]-4,6-dimethoxy-pyrimidine | 330.2 | 2.22 |
| 5 | 1-(3-nitro-2-pyridyl)-4-norbornan-2-yl-piperazine | 303.2 | 1.74 |
| 6 | 2-[4-(5-bicyclo[2.2.1]hept-2-enylmethyl)piperazin-1-yl]nicotinamide | 313.2 | 0.61 |
| 7 | 1-(3-chloro-2-pyridyl)-4-norbornan-2-yl-piperazine | 291.9 | 2.06 |
| 8 | 2-[4-(norbornan-2-ylmethyl)piperazin-1-yl]-6-(trifluoromethyl)nicotinonitrile | 365.1 | 2.41 |
| 9 | 1-[1-(3-bicyclo[3.2.1]octyl)-4-piperidyl]-1H-benzotriazole | 311.2 | 2.15 |
| 10 | 2-(4-norbornan-2-ylpiperazin-1-yl)nicotinamide | 301.4 | 0.47 |
| 11 | 3-[4-(4-cyano-6-phenyl-pyridazin-3-yl)piperazin-1-yl]-8-azabicyclo[3.2.1]octane-8-carboxylic acid ethyl ester | 447.4 | 2.19 |
| 12 | 3-[4-(3-cyano-2-pyridyl)piperazin-1-yl]-8-azabicyclo[3.2.1]octane-8-carboxylic acid ethyl ester | 370.2 | 1.8 |
| 13 | 6-[4-(5-bicyclo[2.2.1]hept-2-enylmethyl)piperazin-1-yl]nicotinonitrile | 295 | 2.12 |
| 14 | 6-[4-(norbornan-2-ylmethyl)piperazin-1-yl]nicotinamide | 315.3 | 1.56 |
| 15 | 1-(5-bicyclo[2.2.1]hept-2-enylmethyl)-4-(6-methyl-2-pyridyl)-piperazine | 284.2 | 0.85 |
| 16 | 3-[14-(5-bicyclo[2.2.1]hept-2-enylmethyl)piperazin-l-yl]-2,5-dimethyl-pyrazine | 299.2 | 1.79 |
| 17 | 2-[4-(5-bicyclo[2.2.1]hept-2-enylmethyl)piperazin-1-yl]-3-methyl-pyrazine | 285.2 | 1.76 |
| 18 | 1-norbornan-2-yl-4-(4-pyridyl)piperazine | 258.2 | 0.38 |
| 19 | 6-(4-norbornan-2-ylpiperazin-1-yl)nicotinonitrile | 283 | 1.6 |
| 20 | 2-[4-(5-bicyclo[2.2.1]hept-2-enylmethyl)piperazin-l-yl]-3-methyl-pyridine | | |
| 21 | 1-(5-bicyclo[2.2.1]hept-2-enylmethyl)-4-(6-chloro-2-pyridyl)-piperazine | 304 | 2.47 |

TABLE 2-continued

| No. | Name | LCMS Plus | LCMS RT |
|---|---|---|---|
| 22 | 5-ethyl-2-[4-(norbornan-2-ylmethyl)piperazin-1-yl]-pyrimidine | 301.5 | 2.2 |
| 23 | 3-[4-(4-bicyclo[3.2.1]octylmethyl)piperazin-1-yl]pyrazine-2-carbonitrile | 311.2 | 2.91 |
| 24 | 3-[4-[3-cyano-6-(trifluoromethyl)-2-pyridyl]piperazin-1-yl]-8-azabicyclo[3.2.1]octane-8-carboxylic acid ethyl ester | 438.5 | 2.17 |
| 25 | 3-[4-(4-pyridyl)piperazin-1-yl]-8-azabicyclo[3.2.1]octane-8-carboxylic acid ethyl ester | 345.2 | 0.73 |
| 26 | 1-(5-bicyclo[2.2.1]hept-2-enylmethyl)-4-(3,5-dichloro-4-pyridyl)-piperazine | 338.2 | 2.3 |
| 27 | 2-[4-(3-bicyclo[3.2.1]octyl)piperazin-1-yl]nicotinonitrile | 297.2 | 1.86 |
| 28 | 3-[4-[5-(trifluoromethyl)-2-pyridyl]piperazin-1-yl]-8-azabicyclo[3.2.1]octane-8-carboxylic acid ethyl ester | 413 | 2.34 |
| 29 | 3-[4-(1H-benzotriazol-1-yl)-1-piperidyl]-8-azabicyclo[3.2.1]octane-8-carboxylic acid ethyl ester | 384.2 | 1.97 |
| 30 | 3-[4-(3-fluoro-2-pyridyl)piperazin-1-yl]-8-azabicyclo[3.2.1]octane-8-carboxylic acid ethyl ester | 363.3 | 1.82 |
| 31 | 6-methyl-2-(4-norbornan-2-ylpiperazin-1-yl)-nicotinonitrile | 297.2 | 1.88 |
| 32 | 2-(4-norbornan-2-ylpiperazin-1-yl)nicotinonitrile | 283.2 | 1.63 |
| 33 | 3-[4-(3-cyano-5-phenyl-2-pyridyl)piperazin-1-yl]-8-azabicyclo[3.2.1]octane-8-carboxylic acid ethyl ester | 446.3 | 2.42 |
| 34 | 6-[4-(5-bicyclo[2.2.1]hept-2-enylmethyl)piperazin-1-yl]nicotinonitrile | 295 | 2.21 |
| 35 | 1-(3-bicyclo[3.2.1]octyl)-4-(4-pyridyl)piperazine | 272.2 | 1.7 |
| 36 | 3-[4-(5-carbamoyl-2-pyridyl)piperazin-1-yl]-8-azabicyclo[3.2.1]octane-8-carboxylic acid ethyl ester | 388.5 | 1.41 |
| 37 | 1-[1-(5-bicyclo[2.2.1]hept-2-enylmethyl)-4-piperidyl]-1H-benzotriazole | 309.4 | 1.88 |
| 38 | 3-[[4-(3-cyanopyrazin-2-yl)piperazin-1-yl]methyl]-8-azabicyclo[3.2.1]octane-8-carboxylic acid ethyl ester | 384.23 | 1.98 |
| 39 | 2-[4-(5-bicyclo[2.2.1]hept-2-enylmethyl)piperazin-1-yl]pyrazine | 271.3 | 1.84 |
| 40 | 2,5-dimethyl-3-(4-norbornan-2-ylpiperazin-1-yl)-pyrazine | 287 | 1.48 |
| 41 | 1-(5-bicyclo[2.2.1]hept-2-enylmethyl)-4-(4-pyridyl)piperazine | 270.2 | 0.51 |
| 42 | 2-[4-(5-bicyclo[2.2.1]hept-2-enylmethyl)piperazin-1-yl]nicotinonitrile | 295.2 | 1.85 |
| 43 | 3-(4-norbornan-2-ylpiperazin-1-yl)pyrazine-2-carbonitrile | 284.4 | 1.44 |
| 44 | 2-(4-norbornan-2-ylpiperazin-1-yl)pyrazine | 259.1 | 0.88 |
| 45 | 3-[4-(3-cyanopyrazin-2-yl)piperazin-1-yl]-8-azabicyclo[3.2.1]octane-8-carboxylic acid ethyl ester | 413 | 2.34 |
| 46 | 2-[4-(norbornan-2-ylmethyl)piperazin-1-yl]-5-phenyl-nicotinonitrile | 373.1 | 2.58 |
| 47 | 1-(5-bicyclo[2.2.1]hept-2-enylmethyl)-4-[5-(trifluoromethyl)-2-pyridyl]-piperazine | 338.2 | 2.46 |
| 48 | 1-(5-bicyclo[2.2.1]hept-2-enylmethyl)-4-(2-pyridyl)piperazine | 270.3 | 0.8 |
| 49 | 3-[4-(3-sulfamoyl-4-pyridyl)piperazin-1-yl]-8-azabicyclo[3.2.1]octane-8-carboxylic acid ethyl ester | 424.3 | 1.56 |
| 50 | 1-(1-norbornan-2-yl-4-piperidyl)-1H-benzotriazole | 297 | 1.69 |
| 51 | 3-[4-(5-acetyl-2-pyridyl)piperazin-1-yl]-8-azabicyclo[3.2.1]octane-8-carboxylic acid ethyl ester | 387.3 | 1.78 |
| 52 | 1-(5-bicyclo[2.2.1]hept-2-enylmethyl)-4-(3-chloro-2-pyridyl)-piperazine | 303.9 | 2.34 |
| 53 | 2-[4-(5-bicyclo[2.2.1]hept-2-enylmethyl)piperazin-1-yl]-6-(trifluoromethyl)nicotinonitrile | 363.2 | 2.35 |
| 54 | 2-[1-(5-bicyclo[2.2.1]hept-2-enylmethyl)-4-piperidyl]nicotinonitrile | 294.2 | 2.11 |
| 55 | 4-[4-(norbornan-2-ylmethyl)piperazin-1-yl]pyridine-3-sulfonamide | 351.3 | 1.67 |
| 56 | 3-[4-(4-cyano-2-pyridyl)piperazin-1-yl]-8-azabicyclo[3.2.1]octane-8-carboxylic acid ethyl ester | 370.2 | 1.74 |
| 57 | 3-[4-(4,6-dimethoxypyrimidin-2-yl)-1-piperidyl]-8-azabicyclo[3.2.1]octane-8-carboxylic acid ethyl ester | 405.2 | 2.16 |
| 58 | 3-[4-[6-chloro-3-cyano-4-(trifluoromethyl)-2-pyridyl]piperazin-1-yl]-8-azabicyclo[3.2.1]octane-8-carboxylic acid ethyl ester | 472.4 | 2.36 |
| 59 | 3-[4-(norbornan-2-ylmethyl)piperazin-1-yl]-6-phenyl-pyridazine-4-carbonitrile | 374.3 | 2.42 |
| 60 | 1-(3-methyl-2-pyridyl)-4-norbornan-2-yl-piperazine | 272.2 | 0.72 |
| 61 | 1-(2-bicyclo[3.2.1]octyl)-4-(4-pyridyl)piperazine | 272.2 | 1.49 |
| 62 | 2-[4-(5-bicyclo[2.2.1]hept-2-enylmethyl)piperazin-1-yl]-6-methyl-nicotinonitrile | 309.4 | 2.09 |
| 63 | 2-methyl-3-(4-norbornan-2-ylpiperazin-1-yl)-pyrazine | 273.2 | 1.28 |
| 64 | 2-[4-(4-bicyclo[3.2.1]octylmethyl)piperazin-1-yl]nicotinonitrile | 310.216 | 2.39 |
| 65 | 1-norbornan-2-yl-4-(2-pyridyl)piperazine | 258.3 | 0.46 |

TABLE 2-continued

| No. | Name | LCMS Plus | LCMS RT |
|---|---|---|---|
| 66 | 3-[4-(5-cyano-2-pyridyl)piperazin-1-yl]-8-azabicyclo[3.2.1]octane-8-carboxylic acid ethyl ester | 370 | 1.82 |
| 67 | 3-[4-(5-ethylpyrimidin-2-yl)piperazin-1-yl]-8-azabicyclo[3.2.1]octane-8-carboxylic acid ethyl ester | 374.2 | 2 |
| 68 | 3-[[4-(3-cyano-2-pyridyl)piperazin-1-yl]methyl]-8-azabicyclo[3.2.1]octane-8-carboxylic acid ethyl ester | 383.23 | 1.86 |
| 69 | 1-(5-bicyclo[2.2.1]hept-2-enylmethyl)-4-[3-(trifluoromethyl)-2-pyridyl]-piperazine | 338.4 | 2.19 |
| 70 | 3-[4-(5-bicyclo[2.2.1]hept-2-enylmethyl)piperazin-1-yl]pyrazine-2-carbonitrile | 296.2 | 1.77 |
| 71 | 2-(4-norbornan-2-ylpiperazin-1-yl)pyrimidine | 259.1 | 0.94 |
| 72 | 4,6-dimethyl-2-(4-norbornan-2-ylpiperazin-1-yl)-pyrimidine | 287.2 | 1.57 |
| 73 | 6-methyl-2-[4-(norbornan-2-ylmethyl)piperazin-1-yl]-5-phenyl-nicotinonitrile | 387.3 | 2.71 |
| 74 | 1-(5-bicyclo[2.2.1]hept-2-enylmethyl)-4-[3-chloro-5-(trifluoromethyl)-2-pyridyl]-piperazine | 372.2 | 2.43 |
| 75 | 1-(2-adamantyl)-4-(4-pyridyl)piperazine | 298.2 | 0.61 |
| 76 | 2-[4-(5-bicyclo[2.2.1]hept-2-enylmethyl)piperazin-1-yl]pyrimidine | 271.3 | 1.97 |
| 77 | 1-(6-methyl-2-pyridyl)-4-norbornan-2-yl-piperazine | 272.2 | 0.45 |
| 78 | 3-[4-(3-cyano-4,6-dimethyl-2-pyridyl)piperazin-1-yl]-8-azabicyclo[3.2.1]octane-8-carboxylic acid ethyl ester | 398.2 | 2.25 |

Example 5

Functional Mobilization of Intracellular Calcium to Determine Muscarinic Receptor Activity CHO cells expressing muscarinic receptors (M1 to M5) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat#12430-054), containing 25 mM Hepes and supplemented with Fetal Bovine Serum (Hyclone, cat#SH30071.03), 0.1 mM of MEM non-essential amino acids (GIBCO, Cat#11140-050), 1 mM MEM Sodium Pyruvate (GIBCO Cat#11360-070) and 100 units/ml of Penicillin G and 100 µg/ml of Streptomycin (GIBCO Cat#15140-122). The recombinant muscarinic receptor cell lines are grown under antibiotic pressure with media containing 25 µg/ml zeocin and 500 µg/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Versene (GIBCO Cat#15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 µl/well of Fluo-3 AM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 µl/well of this solution after the wash. Alternatively, cells can be loaded with the calcium indicator from Molecular Devices (Calcium 3 Assay Reagents, Cat #R7181) adding 5 µl of a 5× solution dye in Bath 1 containing 1 mM Probenecid (10 ml per dye flask cat#R7182 to generate a solution 20×) to 20 µl of the same buffer. After loading for 60 min. the experiment can be run without having to remove the dye.

Compounds are prepared at a 2× fold concentration in a 96-well plate (round bottom, Costar Corning cat#3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 µl compound/well) to the cell assay plate (containing 25 µl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 µl compound/well) to the assay plate and pre-incubated for 15 min prior to adding 25 µl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family (M1 to M5 cells).

The compounds of the present invention were found to selectively modulate the muscarinic receptors selectively over the other receptor types.

Example 6

β-Lactamase Assay to Determine Muscarinic Receptor Activity

CHO cells expressing muscarinic receptors (M1 to M5) and containing a gene reporter system β-Lactamase) with transcriptional control mediated by calcium release (NFAT activation). See Zlokarnik, G; Negulescu, P. A.; Knapp, T. E.; Mere, L; Burres, N; Feng, L; Whitney, M; Roemer, K; Tsien, R. Y. Quantitation of transcription and clonal selection of single living cells with β-lactamase as reporter. Science, 1998

Jan. 2, 279(5347):84-8. The cells are grown as monolayers in tissue culture flasks at 37° C. in a humidified atmosphere containing 5% $CO_2$ and passaged every 3-5 days. The growth media is Dulbecco's modified eagles medium (DMEM, Gibco Cat#12430-054), containing 25 mM Hepes and supplemented with 10% Fetal Bovine Serum (Hyclone, cat#SH30071.03), 0.1 mM of MEM non-essential amino acids (GIBCO, Cat#11140-050), 1 mM MEM Sodium Pyruvate (GIBCO Cat#11360-070) and 100 units/ml of Penicillin G and 100 μg/ml of Streptomycin (GIBCO Cat#15140-122). The recombinant muscarinic receptor cell lines are grown under antibiotic pressure with media containing 25 μg/ml zeocin and 500 μg/ml G418 (M1-CHO), 4 μg/ml puromycin, 50 μg/ml zeocin and 2.5 μg/ml blasticidin (M2 and M4-CHO) or 50 μg/ml zeocin and 4 μg/ml puromycin (M3 and M5-CHO).

Cells are harvested at 80-90% confluence using Accutase (Innovative Cell Technologies, Inc. Cat#AT104), collected by centrifugation and seeded for 2-6 hours at a density of 15,000-20,000 cells/well in black-walled, clear-bottomed 384-well plates (BD Biocoat, poly-D-lysine, Cat#356663). Media is replaced with DMEM+1% Fetal Bovine Serum and incubated for another 12-18 hrs prior to running the β-Lactamase assay. The day of the experiment, compounds are prepared at a 1× fold concentration in a 96-well plate (round bottom, Costar Corning cat#3656), by reconstituting the pre-spotted compounds in DMEM+1% FBS. The final concentration of DMSO is 0.5%, and the amount of DMSO is normalized across the assay plate. To determine an agonist action of the compounds on muscarinic receptors, the reconstituted compounds are added (25 μl compound/well) to the cell assay plate (where the media has been removed) using the multichannel robotic system, Multimek 96 (Beckman). The compounds are incubated with the cells for 3 hours at 37° C., 5% $CO_2$ to allow for expression of the reporter gene β-Lactamase.

After 3 hours, 5 μl of 6× fold concentrated CCF2/AM dye are added to the assay plates and incubated at room temperature for 1 hour. Fluorescent emission at two wavelengths (460 nm and 530 nm) is determined using the CytoFluor Series 4000 (PerSeptive Biosystems) and the calculations for reporter gene expression determined as specified in prior publications {Zlokarnik, G; Negulescu, P. A.; Knapp, T. E.; Mere, L; Burres, N; Feng, L; Whitney, M; Roemer, K; Tsien, R. Y. Quantitation of transcription and clonal selection of single living cells with β-lactamase as reporter. Science, 1998 Jan. 2, 279(5347):84-8.}

The potency, efficacy and selectivity of the muscarinic compounds were evaluated by screening the compound activity across the whole family (M1 to M5 cells). Compounds were also screened for activity on other proteins such as other GPCRs and ion channels to determine selectivity on M4 receptors.

The compounds of the present invention were found to modulate the muscarinic receptors selectively over the other receptor types.

Table 3 contains activity data for the compounds listed in Tables 1 and 2. The symbol "+++" refers to compounds which exhibited muscarinic modulation activity for at least one muscarinic receptor, M1, M2, M3, M4, at a concentration of less than 5 μM. The symbol "++" refers to compounds which exhibited muscarinic modulation activity for at least one muscarinic receptor, M1, M2, M3, M4, at a concentration of between 30 μM and 5 μM. The symbol "+" refers to compounds which exhibited muscarinic modulation activity for at least one muscarinic receptor, M1, M2, M3, M4, at a concentration of greater than 30 μM. The symbol "−" refers to compounds which were not assayed or did not exhibit muscarinic modulation activity for at least one muscarinic receptor, M1, M2, M3, M4, at the concentration at which the assay was performed.

TABLE 3

| No. | ACTIVITY |
| --- | --- |
| 1 | ++ |
| 2 | ++ |
| 3 | + |
| 4 | +++ |
| 5 | + |
| 6 | − |
| 7 | +++ |
| 8 | − |
| 9 | − |
| 10 | − |
| 11 | + |
| 12 | +++ |
| 13 | +++ |
| 14 | − |
| 15 | ++ |
| 16 | +++ |
| 17 | +++ |
| 18 | ++ |
| 19 | ++ |
| 20 | +++ |
| 21 | − |
| 22 | − |
| 23 | − |
| 24 | +++ |
| 25 | +++ |
| 26 | − |
| 27 | + |
| 28 | +++ |
| 29 | +++ |
| 30 | +++ |
| 31 | ++ |
| 32 | + |
| 33 | + |
| 34 | +++ |
| 35 | ++ |
| 36 | +++ |
| 37 | + |
| 38 | +++ |
| 39 | + |
| 40 | − |
| 41 | +++ |
| 42 | +++ |
| 43 | − |
| 44 | ++ |
| 45 | + |
| 46 | ++ |
| 47 | + |
| 48 | ++ |
| 49 | +++ |
| 50 | ++ |
| 51 | +++ |
| 52 | ++ |
| 53 | + |
| 54 | +++ |
| 55 | ++ |
| 56 | +++ |
| 57 | +++ |
| 58 | − |
| 59 | + |
| 60 | + |
| 61 | − |
| 62 | +++ |
| 63 | + |
| 64 | + |
| 65 | ++ |
| 66 | +++ |
| 67 | +++ |
| 68 | +++ |
| 69 | +++ |
| 70 | +++ |
| 71 | ++ |
| 72 | − |

TABLE 3-continued

| No. | ACTIVITY |
|-----|----------|
| 73  | −        |
| 74  | −        |
| 75  | ++       |
| 76  | +++      |
| 77  | −        |
| 78  | ++       |

The invention claimed is:

1. A compound of formula (IV):

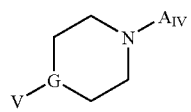

or a pharmaceutically acceptable salt thereof, wherein $A_{IV}$ is adamantanyl, adamantanylmethyl, or

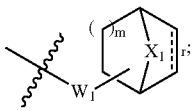

Bond r is a single or double bond;

Each $X_1$ is independently selected from $CH_2$, $CH_2$—$CH_2$, or $NR^{400}$,

Each $W_1$ is independently selected from a bond or —$(CH_2)_i$—,

Each $R^5$ is independently a phenyl, indenyl, naphthalenyl, tetrahydronaphthyl, furyl, thiophenyl, pyrrolyl, oxazolyl, thazolyl, imidazolyl, pyrazolyl, pyridyl, pyrimidyl, pyrazyl, indolyl, isoindolyl, 3H-indolyl, indolinyl, benzo[b]furyl, benzo[b]thiophenyl, quinolinyl, isoquinolinyl, cycloaliphatic, or heterocyclic ring, each optionally including 1 to 3 $R^{100}$ substituents;

Each $R^6$ is independently H or aliphatic optionally substituted with $R^7$;

Each $R^7$ is independently a phenyl, indenyl, naphthalenyl, tetrahydronaphthyl, furyl, thiophenyl, pyrrolyl, oxazolyl, thazolyl, imidazolyl, pyrazolyl, pyridyl, pyrimidyl, pyrazyl, indolyl, isoindolyl, 3H-indolyl, indolinyl, benzo[b]furyl, benzo[b]thiophenyl, quinolinyl, isoquinolinyl, cycloaliphatic, or heterocyclic ring, each optionally substituted with up to 2 substituents independently selected from H, $(C_1-C_6)$-straight or branched alkyl, $(C_2-C_6)$ straight or branched alkenyl or alkynyl, 1,2-methylenedioxy, 1,2-ethylenedioxy, or —$(CH_2)_n$—Z;

Each Z is independently selected from halo, —CN, —$NO_2$, —$CF_3$, —$OCF_3$, —OH, —S-aliphatic, —S(O)-aliphatic, —$S(O)_2$-aliphatic, —COOH, —C(O)O(-aliphatic), or —O-aliphatic;

G is N;

V is

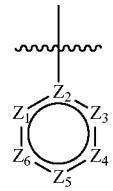

Each Z2 is independently a carbon atom;
Each Z4 and Z6 is independently —C(H)= or —C($R^{100}$)=;
Each Z1, Z3, and Z5 is independently —N=, —C(H)=, or —C($R^{200}$)=,
provided
a) that one of Z1, Z3, and Z5 is —N=;
d) when Z4 or Z6 is —C($R^{100}$)=, that (i) one of Z1 and Z3 is —C($R^{100}$)=, (ii) Z5 is —C($R^{200}$)=, or (iii) both Z4 and Z6 are —C($R^{100}$)=;
Each $R^{100}$ is independently is —(($C_1$-$C_4$)aliphatic)$_p$-Y2;
Y2 is halo, —CN, —$NO_2$, —$CF_3$, —$OCF_3$, —$SR_{600}$, —$S(O)R_{600}$, —$S(O)_2R_{600}$, —$S(O)_2NR_{600}$, —$COOR_{600}$, —$C(O)N(R_{600})_2$, or —$OR_{600}$; or
Each $R^{200}$ is independently $R^{100}$ or phenyl optionally substituted with 1-3 halo, —CN, —$NO_2$, —$CF_3$, —$OCF_3$, —OH;
Each $R^{400}$ is independently $OR^5$, $OR^6$, $S(O)R^6$, $S(O)R^5$, $S(O)_2R^6$, $S(O)_2R^5$, $S(O)_2N(R^6)_2$, $S(O)_2N(R^5)_2$, $S(O)_2NR^5R^6$, $S(O)_3R^6$, $S(O)_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, and $C(NOR^5)R^5$;
Each $R_{600}$ is independently H or aliphatic optionally substituted with 1-3 substituents selected from halo, —CN, —$NO_2$, —$CF_3$, —$OCF_3$, or —OH;
Each x is 1;
Each i is 0, 1 2, or 3;
Each m is independently 1 or 2;
Each p is independently 0 or 1; and
further provided that
when G is N and $A_{IV}$ is azabicyclo[3.2.1]octane-8-carboxylic acid t-butyl ester, then V is not-pyridine-2-yl-5-carboxylic acid.

2. The compound according to claim 1, wherein $A_{IV}$ is selected from:

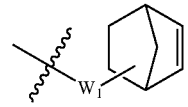

(ia)

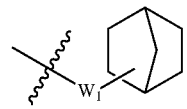

(ib)

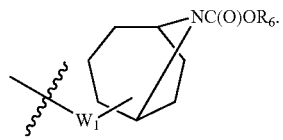

(ic)

3. The compound according to claim 2, wherein $A_{IV}$ is (ia).

4. The compound according to claim 3, wherein $A_{IV}$ is

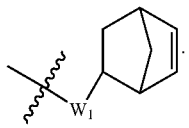

5. The compound according to claim 4, wherein $W_1$ is a bond or —$CH_2$—.

6. The compound according to claim 2, wherein $A_{IV}$ is (ib).

7. The compound according to claim 6, wherein $A_{IV}$ is

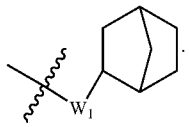

8. The compound according to claim 7, wherein $W_1$ is a bond or —$CH_2$—.

9. The compound according to claim 2, wherein $A_{IV}$ is (ic).

10. The compound according to claim 2, wherein $W_1$ is a bond or —$CH_2$—.

11. The compound according to claim 1, wherein $W_1$ is a bond or —$CH_2$—.

12. The compound according to claim 1, wherein $A_{IV}$ is

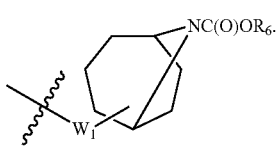
(ic)

13. The compound according to claim 12, wherein $W_1$ is a bond or $CH_2$.

14. The compound according to claim 12, wherein $A_{IV}$ is

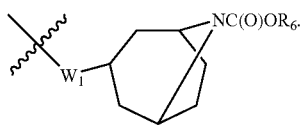
(ic)

15. The compound according to claim 14, wherein $W_1$ is a bond.

16. The compound according to claim 12, wherein $R_6$ is aliphatic optionally substituted with $R^7$.

17. The compound according to claim 16, wherein $R_6$ is alkyl optionally, substituted with $R^7$.

18. The compound according to claim 17, wherein $R_6$ is unsubstituted alkyl.

19. The compound according to claim 1, wherein $A_{IV}$ is adamantyl or adamantylmethyl.

20. The compound according to claim 1, wherein $Z_1$ is —N=.

21. The compound according to claim 20, wherein $Z_3$ is —C($R^{100}$)=.

22. The compound according to claim 21, wherein $R^{100}$ is halo, nitro, —CN, —S(O)$NH_2$, —$CF_3$, alkoxy, acyl, —C(O)$NH_2$, or aliphatic.

23. The compound according to claim 1, wherein $Z_5$ is —N=.

24. The compound according to claim 1, wherein ring V is selected from:

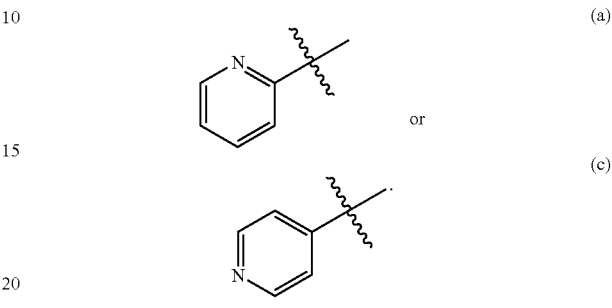

25. The compound according to claim 24, wherein each of V rings (a) or (c) is substituted with one $R^{100}$ substituent ortho or para relative to the point of attachment between ring V and the piperazine or piperidine ring, or one $R^{100}$ substituent ortho, meta, or para relative to the point of attachment between ring V and the piperazine or piperidine ring and one $R^{100}$ substituent meta relative to the point of attachment between ring V and the piperazine or piperidine ring.

26. The compound according to claim 25, wherein each $R^{100}$ is independently halo, nitro, —CN, S(O)$_2$$NH_2$—, —$CF_3$, alkoxy, acyl, —C(O)$NH_2$, or aliphatic.

27. The compound according to claim 26, wherein ring V is 3-cyano-2-pyridyl or 5-cyano-2-pyridyl.

28. A compound according to claim 1, wherein the compound is selected from
1-(5-bicyclo[2.2.1]hept-2-enylmethyl)-4-(3-nitro-2-pyridyl)-piperazine;
2-[4-(2-adamantyl)piperazin-1-yl]nicotinonitrile;
2-(4-norbornan-2-ylpiperazin-1-yl)-6-(trifluoromethyl)nicotinonitrile;
1-(3-nitro-2-pyridyl)-4-norbornan-2-yl-piperazine;
2-[4-(5-bicyclo[2.2.1]hept-2-enylmethyl)piperazin-1-yl]nicotinamide;
1-(3-chloro-2-pyridyl)-4-norbornan-2-yl-piperazine;
2-[4-(norbornan-2-ylmethyl)piperazin-1-yl]-6-(trifluoromethyl)nicotinonitrile;
2-(4-norbornan-2-ylpiperazin-1-yl)nicotinamide;
3-[4-(3-cyano-2-pyridyl)piperazin-1-yl]-8-azabicyclo[3.2.1]octane-8-carboxylic acid ethyl ester;
6-[4-(5-bicyclo[2.2.1]hept-2-enylmethyl)piperazin-1-yl]nicotinonitrile;
6-[4-(norbornan-2-ylmethyl)piperazin-1-yl]nicotinamide;
1-(5-bicyclo[2.2.1]hept-2-enylmethyl)-4-(6-methyl-2-pyridyl)-piperazine;
1-norbornan-2-yl-4-(4-pyridyl)piperazine;
6-(4-norbornan-2-ylpiperazin-1-yl)nicotinonitrile;
2-[4-(5-bicyclo[2.2.1]hept-2-enylmethyl)piperazin-1-yl]-3-methyl-pyridine;
1-(5-bicyclo[2.2.1]hept-2-enylmethyl)-4-(6-chloro-2-pyridyl)-piperazine;
3-[4-[3-cyano-6-(trifluoromethyl)-2-pyridyl]piperazin-1-yl]-8-azabicyclo[3.2.1]octane-8-carboxylic acid ethyl ester;
3-[4-(4-pyridyl)piperazin-1-yl]-8-azabicyclo[3.2.1]octane-8-carboxylic acid ethyl ester;

1-(5-bicyclo[2.2.1]hept-2-enylmethyl)-4-(3,5-dichloro-4-pyridyl)-piperazine;
2-[4-(3-bicyclo[3.2.1]octyl)piperazin-1-yl]nicotinonitrile;
3-[4-[5-(trifluoromethyl)-2-pyridyl]piperazin-1-yl]-8-azabicyclo[3.2.1]octane-8-carboxylic acid ethyl ester;
3-[4-(3-fluoro-2-pyridyl)piperazin-1-yl]-8-azabicyclo[3.2.1]octane-8-carboxylic acid ethyl ester;
6-methyl-2-(4-norbornan-2-ylpiperazin-1-yl)-nicotinonitrile;
2-(4-norbornan-2-ylpiperazin-1-yl)nicotinonitrile;
3-[4-(3-cyano-5-phenyl-2-pyridyl)piperazin-1-yl]-8-azabicyclo[3.2.1]octane-8-carboxylic acid ethyl ester;
6-[4-(5-bicyclo[2.2.1]hept-2-enylmethyl)piperazin-1-yl]nicotinonitrile;
1-(3-bicyclo[3.2.1]octyl)-4-(4-pyridyl)piperazine;
3-[4-(5-carbamoyl-2-pyridyl)piperazin-1-yl]-8-azabicyclo[3.2.1]octane-8-carboxylic acid ethyl ester;
1-(5-bicyclo[2.2.1]hept-2-enylmethyl)-4-(4-pyridyl)piperazine;
2-[4-(5-bicyclo[2.2.1]hept-2-enylmethyl)piperazin-1-yl]nicotinonitrile;
2-[4-(norbornan-2-ylmethyl)piperazin-1-yl]-5-phenyl-nicotinonitrile;
1-(5-bicyclo[2.2.1]hept-2-enylmethyl)-4-[5-(trifluoromethyl)-2-pyridyl]-piperazine;
1-(5-bicyclo[2.2.1]hept-2-enylmethyl)-4-(2-pyridyl)piperazine;
3-[4-(3-sulfamoyl-4-pyridyl)piperazin-1-yl]-8-azabicyclo[3.2.1]octane-8-carboxylic acid ethyl ester;
3-[4-(5-acetyl-2-pyridyl)piperazin-1-yl]-8-azabicyclo[3.2.1]octane-8-carboxylic acid ethyl ester;
1-(5-bicyclo[2.2.1]hept-2-enylmethyl)-4-(3-chloro-2-pyridyl)-piperazine;
2-[4-(5-bicyclo[2.2.1]hept-2-enylmethyl)piperazin-1-yl]-6-(trifluoromethyl)nicotinonitrile;
2-[1-(5-bicyclo[2.2.1]hept-2-enylmethyl)-4-piperidyl]nicotinonitrile;
4-[4-(norbornan-2-ylmethyl)piperazin-1-yl]pyridine-3-sulfonamide;
3-[4-(4-cyano-2-pyridyl)piperazin-1-yl]-8-azabicyclo[3.2.1]octane-8-carboxylic acid ethyl ester;
3-[4-[6-chloro-3-cyano-4-(trifluoromethyl)-2-pyridyl]piperazin-1-yl]-8-azabicyclo[3.2.1]octane-8-carboxylic acid ethyl ester;
1-(3-methyl-2-pyridyl)-4-norbornan-2-yl-piperazine;
1-(2-bicyclo[3.2.1]octyl)-4-(4-pyridyl)piperazine;
2-[4-(5-bicyclo[2.2.1]hept-2-enylmethyl)piperazin-1-yl]-6-methyl-nicotinonitrile;
2-[4-(4-bicyclo[3.2.1]octylmethyl)piperazin-1-yl]nicotinonitrile;
1-norbornan-2-yl-4-(2-pyridyl)piperazine;
3-[4-(5-cyano-2-pyridyl)piperazin-1-yl]-8-azabicyclo[3.2.1]octane-8-carboxylic acid ethyl ester;
3-[[4-(3-cyano-2-pyridyl)piperazin-1-yl]methyl]-8-azabicyclo[3.2.1]octane-8-carboxylic acid ethyl ester;
1-(5-bicyclo[2.2.1]hept-2-enylmethyl)-4-[3-(trifluoromethyl)-2-pyridyl]-piperazine;
6-methyl-2-[4-(norbornan-2-ylmethyl)piperazin-1-yl]-5-phenyl-nicotinonitrile;
1-(5-bicyclo[2.2.1]hept-2-enylmethyl)-4-[3-chloro-5-(trifluoromethyl)-2-pyridyl]-piperazine;
1-(2-adamantyl)-4-(4-pyridyl)piperazine;
1-(6-methyl-2-pyridyl)-4-norbornan-2-yl-piperazine; and
3-[4-(3-cyano-4,6-dimethyl-2-pyridyl)piperazin-1-yl]-8-azabicyclo[3.2.1]octane-8-carboxylic acid ethyl ester.

29. A compound according to claim 1, wherein V is

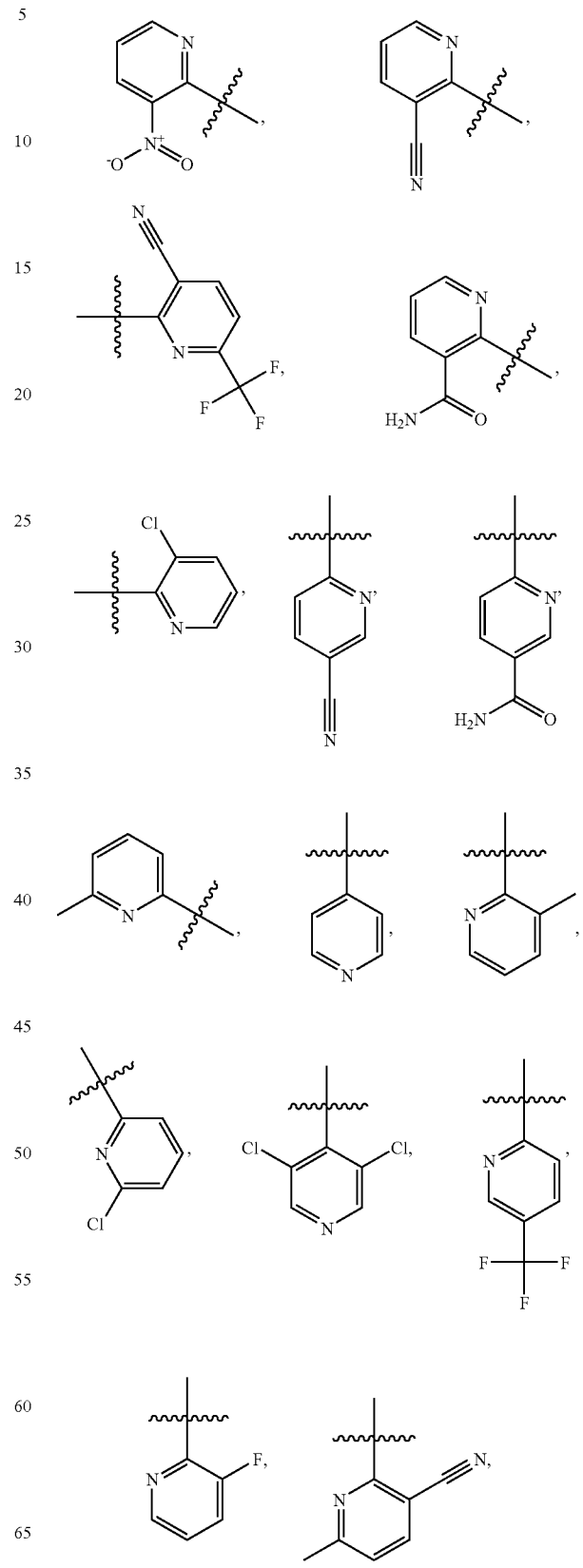

-continued
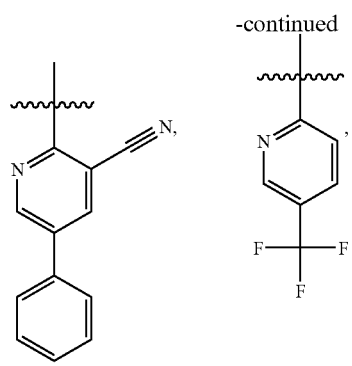 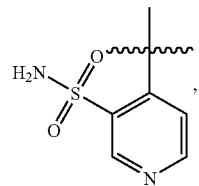
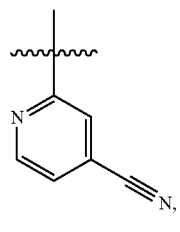 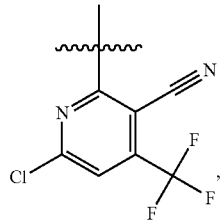
-continued
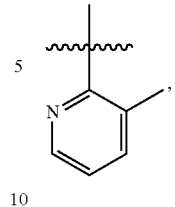 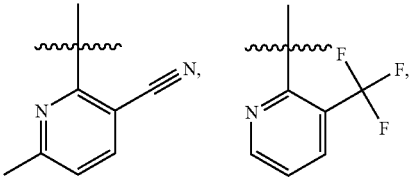
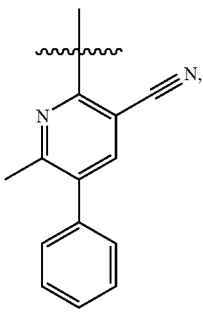 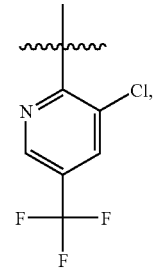
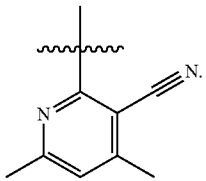
* * * * *